US012799136B2

(12) United States Patent
Xu et al.

(10) Patent No.: US 12,799,136 B2
(45) Date of Patent: Nov. 17, 2026

(54) SUBSTITUTED THIENO[2,3-A]PHENOTHIAZINES FOR THE PREPARATION OF PHOTOTHERAPY MEDICINES

(71) Applicant: Guangzhou Medical University, Guangzhou (CN)

(72) Inventors: Chuanshan Xu, Guangzhou (CN); Houhe Liu, Guangzhou (CN)

(73) Assignee: Guangzhou Medical University, Guangzhou (CN)

( * ) Notice: Subject to any disclaimer, the term of this patent is extended or adjusted under 35 U.S.C. 154(b) by 313 days.

(21) Appl. No.: 18/623,007

(22) Filed: Mar. 31, 2024

(65) Prior Publication Data

US 2024/0327432 A1 Oct. 3, 2024

(30) Foreign Application Priority Data

Mar. 31, 2023 (CN) ......................... 202310334638.8

(51) Int. Cl.

*A61K 31/542* (2006.01)
*C07D 513/04* (2006.01)
*C07D 513/22* (2006.01)

(52) U.S. Cl.

CPC .......... *C07D 513/04* (2013.01); *A61K 31/542* (2013.01)

(58) Field of Classification Search

CPC ............................ A61K 31/542; C07D 513/22
USPC .......................................... 514/224.5; 544/14
See application file for complete search history.

(56) References Cited

FOREIGN PATENT DOCUMENTS

| | | |
|---|---|---|
| CN | 102718730 A | 10/2012 |
| CN | 110317198 A | 10/2019 |
| CN | 117209508 A | 12/2023 |

*Primary Examiner* — Douglas M Willis
(74) *Attorney, Agent, or Firm* — Nitin Kaushik

(57) ABSTRACT

The present invention belongs to the technical field of biomedicine, and particularly relates to thiophene-phenothiazine compounds represented by Formula I, and a synthesis method thereof, as well as application thereof in preparation of phototherapy medicines. The present invention provides thiophene-phenothiazine compounds or pharmaceutically acceptable salts thereof, in the structure of which a thiophene structure is successfully fused to a phenothiazine framework, providing a novel molecular scaffold. The special structure exhibits excellent photodynamic activity, has strong wavelength absorption and good photostability in a near-infrared region, and can efficiently generate ROS under red light, and therefore, the thiophene-phenothiazine compound or the pharmaceutically acceptable salt thereof can be used as a photosensitizer. The thiophene-phenothiazine compounds of the present invention have strong photocytotoxicity and high phototherapeutic indexes, exhibit strong photodynamic anti-tumor activity without obvious side effects.

I

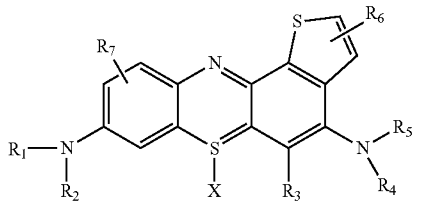

9 Claims, 10 Drawing Sheets

I (1)

(2)

SUBSTITUTED THIENO[2,3-A]PHENOTHIAZINES FOR THE PREPARATION OF PHOTOTHERAPY MEDICINES

CROSS-REFERENCE TO RELATED APPLICATIONS

The application claims priority to Chinese patent application No. 2023103346388, filed on Mar. 31, 2023, the entire contents of which are incorporated herein by reference.

TECHNICAL FIELD

The present invention belongs to the technical field of biomedicine, and particularly relates to thiophene-phenothiazine compounds and a synthesis method thereof, as well as application thereof in preparation of phototherapy medicines.

BACKGROUND

Photodynamic therapy (PDT) has various advantages such as safety, low invasiveness, spatiotemporal accuracy, and strong controllability, and has become an effective and rapidly developing important method for treating benign and malignant diseases. A principle of PDT treatment is that: under light irradiation, a photosensitizer transfers electrons or energy to surrounding molecules through photochemistry, which interact with oxygen to generate a large quantity of highly phototoxic reactive oxygen species (ROS), leading to selective destruction and death of target cells.

At present, photosensitizers commonly used in clinical practice are mainly porphyrin-based photosensitizers which are difficult to prepare and purify, and strong in skin phototoxicity. Phenothiazine photosensitizers are a series of photosensitizers derived from a phenothiazine structure as a parent scaffold. Such photosensitizers have high molar extinction coefficient, good hydrophilicity, good selectivity, and long absorption wavelength, thereby receiving widespread attention of people. Methylene blue (MB) and toluidine blue O(TBO) are two representative phenothiazine photosensitizers that have been clinically applied (structural formulas are shown as below). Further exploration of novel photosensitizers based on the phenothiazine structure is expected to provide novel photosensitive medicines for photodynamic therapy.

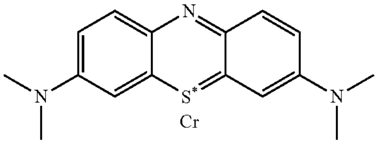

Methylene blue (MB)

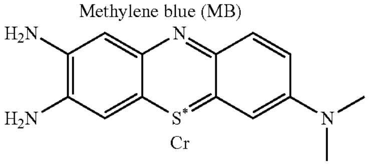

Toluidine blue O (TBO)

SUMMARY

In order to overcome shortcomings and deficiencies in the prior art and give full play to the advantages of the phenothiazine structure, a primary objective of the present invention is to provide thiophene-phenothiazine compounds or pharmaceutically acceptable salts thereof.

Another objective of the present invention is to provide a pharmaceutical composition containing the thiophene-phenothiazine compound.

Yet another objective of the present invention is to provide application of the thiophene-phenothiazine compounds or the pharmaceutically acceptable salts thereof in preparation of phototherapy medicines or lead compounds thereof.

The objectives of the present invention are achieved by the following solutions:

a thiophene-phenothiazine compound or pharmaceutically acceptable salt thereof, having a structural formula shown in a formula I;

I

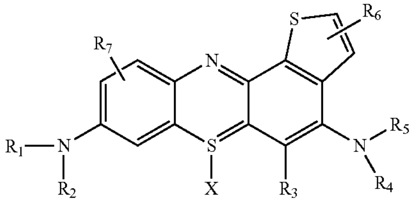

where $R_1$, $R_2$, $R_4$, and $R_5$, which are the same or different, are independently hydrogen, halogen, substituted or unsubstituted linear, branched, or cyclic alkyl chains, substituted or unsubstituted alkoxy groups, substituted or unsubstituted haloalkyl groups, substituted or unsubstituted alkenyl groups, substituted or unsubstituted alkynyl groups, substituted or unsubstituted benzyl groups, substituted or unsubstituted benzyloxy groups, substituted or unsubstituted acyl groups, substituted or unsubstituted sulfonyl groups, substituted or unsubstituted hydrocarboxylcarbonyl groups, substituted or unsubstituted alkylsilyl groups, substituted or unsubstituted phenylsilyl groups, substituted or unsubstituted aryl groups, respectively, or $R_1$ and $R_2$ and N are subjected to cyclization to form substituted or unsubstituted heterocyclic groups or heterocyclic aryl groups, or $R_4$ and $R_5$ and N are subjected to cyclization to form substituted or unsubstituted heterocyclic groups or heterocyclic aryl groups;

$R_3$, $R_6$, and $R_7$, which are the same or different, are independently selected from hydrogen, halogen, hydroxyl groups, carboxyl groups, carbonyl groups, ester groups, cyano groups, nitro groups, amino groups, alkoxy groups, haloalkyl groups, alkyl groups, alkenyl groups, alkynyl groups, cyclic hydrocarbyl groups or aryl groups, respectively; and X is a halogen atom.

Substituted substituents, which are the same or different, are independently selected from hydrogen, halogen, hydroxyl groups, carboxyl groups, carbonyl groups, cyano groups, nitro groups, amino groups, C1-C20 alkyl groups, C1-C20 haloalkyl groups, C3-C20 ester groups, C1-C20 alkenyl groups, C1-C20 alkynyl groups, C6-C20 aryl groups, and C1-C20 hydrocarboxyl groups, respectively.

Further, the thiophene-phenothiazine compound or the pharmaceutically acceptable salt thereof, having the structural formula shown in the formula I, where $R_1$, $R_2$, $R_4$, and $R_5$, which are the same or different, are independently hydrogen, halogen, substituted or unsubstituted C1-C20 linear, branched, or cyclic alkyl chains, substituted or unsubstituted C1-C20 alkoxy groups, substituted or unsubstituted C1-C20 haloalkyl groups, substituted or unsubstituted C3-C20 alkenyl groups, substituted or unsubstituted C3-C20 alkynyl groups, substituted or unsubstituted benzyl groups, substituted or unsubstituted benzyloxy groups, substituted or unsubstituted C1-C20 acyl groups, substituted or unsubstituted C1-C20 sulfonyl groups, substituted or unsubstituted C1-C20 hydrocarboxylcarbonyl groups, substituted or unsubstituted C1-C9 alkylsilyl groups, substituted or unsubstituted phenylsilyl groups, substituted or unsubstituted C6-C20 aryl groups, respectively, or $R_1$ and $R_2$ and N are subjected to cyclization to form substituted or unsubstituted heterocyclic groups or heterocyclic aryl groups, or $R_4$ and $R_5$ and N are subjected to cyclization to form substituted or unsubstituted heterocyclic groups or heterocyclic aryl groups.

Further, the thiophene-phenothiazine compounds or the pharmaceutically acceptable salts thereof, having the structural formula shown in the formula I, where $R_3$, $R_6$ and $R_7$, which are the same or different, are independently selected from hydrogen, halogen, hydroxyl groups, carboxyl groups, carbonyl groups, ester groups, cyano groups, nitro groups, amino groups, C1-C10 alkoxy groups, C1-C10 haloalkyl groups, C1-C10 alkyl groups, C1-C10 alkenyl groups, C1-C10 alkynyl groups, cyclic hydrocarbyl groups, or aryl groups.

Further, the thiophene-phenothiazine compounds or the pharmaceutically acceptable salts thereof, having the structural formula shown in the formula I, where $R_3$, $R_6$ and $R_7$, which are the same or different, are selected from hydrogen, halogen, hydroxyl groups, carboxyl groups, carbonyl groups, ester groups, cyano groups, nitro groups, methoxy groups, amino groups, fluoromethyl groups, methyl groups, ethyl groups, alkenyl groups, alkynyl groups, cyclic hydrocarbyl groups or aryl groups, respectively.

Further, the substituted substituents, which are the same or different, are independently selected from hydrogen, halogen, hydroxyl groups, carboxyl groups, carbonyl groups, cyano groups, nitro groups, amino groups, methyl groups, ethyl groups, propyl groups, methoxy groups, ethoxy groups, fluoromethyl groups, cyclopropyl groups, C1-C20 alkenyl groups, C1-C20 alkynyl groups, and C6-C20 aryl groups, respectively.

Further, one or more hydrogen atoms in $R_1$, $R_2$, $R_4$ and $R_5$, which are the same or different, are substituted with halogen, hydroxyl groups, carboxyl groups, carbonyl groups, ester groups, cyano groups, nitro groups, methoxy groups, amino groups, fluoromethyl groups, methyl groups, ethyl groups, alkenyl groups, alkynyl groups, cyclic hydrocarbyl groups or aryl groups, respectively.

Further, the thiophene-phenothiazine compounds or the pharmaceutically acceptable salts thereof, having a structure shown in a following formula II:

II

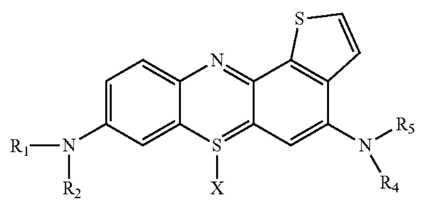

According to the thiophene-phenothiazine compounds or the pharmaceutically acceptable salts thereof of the present invention, a thiophene structure is successfully fused to a phenothiazine framework, providing a novel molecular scaffold. The special structure exhibits excellent photodynamic activity, has strong wavelength absorption and good photostability in a near-infrared region, and can efficiently generate ROS under red light, and therefore, the thiophene-phenothiazine compound or the pharmaceutically acceptable salt thereof can be used as a photosensitizer.

The present invention further provides a pharmaceutical composition, containing the thiophene-phenothiazine compound or the pharmaceutically acceptable salt thereof, and one or more pharmaceutically acceptable carriers or excipients.

Further, the excipient may include at least one of a diluent, a wetting agent, a lubricant, a filler and a preservative.

Further, the pharmaceutical composition is made into various pharmaceutical dosage forms by conventional methods, and the dosage forms include: tablets, capsules, oral liquid, oral lozenges, granules, pills, pellets, paste, suspensions, medicinal liquor, tinctures, cataplasm, drops, patches, smearing preparations, gel, sprays, aerosols, mucosal preparations and injections.

The present invention further provides application of the thiophene-phenothiazine compounds or the pharmaceutically acceptable salts thereof in preparation of phototherapy medicines or lead compounds thereof.

Compared with the prior art, the present invention has the following advantages and beneficial effects:

(1) In the structure of the thiophene-phenothiazine compound of the present invention, a thiophene structure is introduced in the phenothiazine framework, and a novel molecular scaffold is formed.

(2) The thiophene-phenothiazine compound of the present invention has excellent photodynamic activity, has strong wavelength absorption and good photostability in a near-infrared region, and can efficiently generate ROS under red light, and therefore, the thiophene-phenothiazine compound or the pharmaceutically acceptable salt thereof can be used as a photosensitizer.

(3) The thiophene-phenothiazine compound of the present invention has strong photo activity and high phototherapeutic indexes, exhibits strong photodynamic antitumor activity without obvious toxic and side effects, and is expected to become a new generation of clinically applicable novel photosensitizer for preparation of the phototherapy medicines or the lead compounds thereof.

BRIEF DESCRIPTION OF DRAWINGS

To describe the technical solutions in the examples of the present invention more clearly, the following briefly describes the accompanying drawings required for describing the examples. It should be understood that, the following accompanying drawings show merely some examples of the present invention, and therefore should not be regarded as a limitation on the scope. A person of ordinary skill in the art may still derive other related drawings from these accompanying drawings without creative efforts.

DETAILED DESCRIPTION OF THE EMBODIMENTS

The present invention will be described in further detail below with reference to examples, but implementations of the present invention are not limited thereto. Materials involved in the following examples can be commercially obtained unless otherwise specified. Unless otherwise specified, all methods involved are conventional methods.

Figure 1:
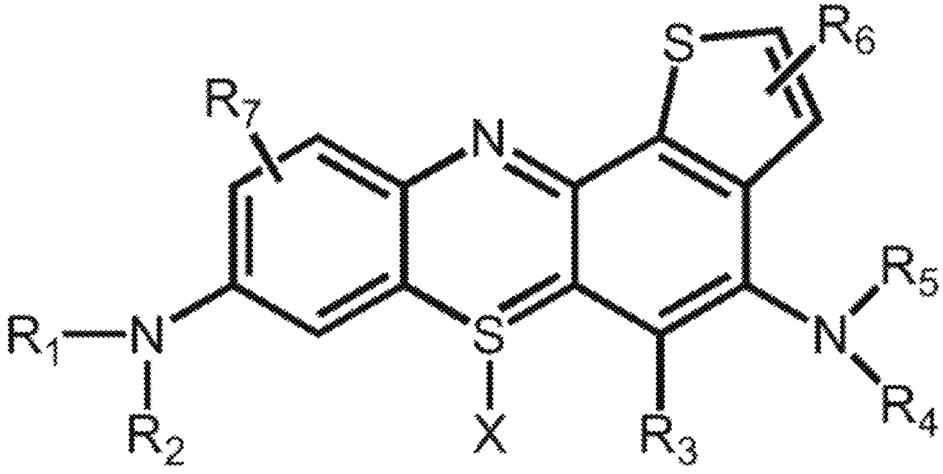
FIG. 1 shows a structural formula of a thiophene-phenothiazine compound of the present invention.

In an implementation, a thiophene-phenothiazine compound or pharmaceutically acceptable salt thereof, having a structural formula shown in FIG. 1, where $R_1$, $R_2$, $R_4$, and $R_5$, which are the same or different, are independently hydrogen, halogen, substituted or unsubstituted linear, branched, or cyclic alkyl chains, substituted or unsubstituted alkoxy groups, substituted or unsubstituted haloalkyl groups, substituted or unsubstituted alkenyl groups, substituted or unsubstituted alkynyl groups, substituted or unsubstituted benzyl groups, substituted or unsubstituted benzyloxy groups, substituted or unsubstituted acyl groups, substituted or unsubstituted sulfonyl groups, substituted or unsubstituted hydrocarboxylcarbonyl groups, substituted or unsubstituted alkylsilyl groups, substituted or unsubstituted phenylsilyl groups, substituted or unsubstituted aryl groups, respectively, or $R_1$ and $R_2$ and N are subjected to cyclization to form substituted or unsubstituted heterocyclic groups or heterocyclic aryl groups, or $R_4$ and $R_5$ and N are subjected to cyclization to form substituted or unsubstituted heterocyclic groups or heterocyclic aryl groups;

$R_3$, $R_6$, and $R_7$, which are the same or different, are independently selected from hydrogen, halogen, hydroxyl groups, carboxyl groups, carbonyl groups, ester groups, cyano groups, nitro groups, amino groups, alkoxy groups, haloalkyl groups, alkyl groups, alkenyl groups, alkynyl groups, cyclic hydrocarbyl groups or aryl groups, respectively; and X is a halogen atom.

Substituted substituents, which are the same or different, are independently selected from hydrogen, halogen, hydroxyl groups, carboxyl groups, carbonyl groups, cyano groups, nitro groups, amino groups, C1-C20 alkyl groups, C1-C20 haloalkyl groups, C3-C20 ester groups, C1-C20 alkenyl groups, C1-C20 alkynyl groups, C6-C20 aryl groups, and C1-C20 hydrocarboxyl groups, respectively.

As a preferred technical solution of the present invention, the thiophene-phenothiazine compound or the pharmaceutically acceptable salt thereof, having the structural formula shown in formula I, where $R_1$, $R_2$, $R_4$, and $R_5$, which are the same or different, are independently hydrogen, halogen, substituted or unsubstituted C1-C20 linear, branched, or cyclic alkyl chains, substituted or unsubstituted C1-C20 alkoxy groups, substituted or unsubstituted C1-C20 haloalkyl groups, substituted or unsubstituted C3-C20 alkenyl groups, substituted or unsubstituted C3-C20 alkynyl groups, substituted or unsubstituted benzyl groups, substituted or unsubstituted benzyloxy groups, substituted or unsubstituted C1-C20 acyl groups, substituted or unsubstituted C1-C20 sulfonyl groups, substituted or unsubstituted C1-C20 hydrocarboxylcarbonyl groups, substituted or unsubstituted C1-C9 alkylsilyl groups, substituted or unsubstituted phenylsilyl groups, substituted or unsubstituted C6-C20 aryl groups, respectively, or $R_1$ and $R_2$ and N are subjected to cyclization to form substituted or unsubstituted heterocyclic groups or heterocyclic aryl groups, or $R_4$ and $R_5$ and N are subjected to cyclization to form substituted or unsubstituted heterocyclic groups or heterocyclic aryl groups.

As a preferred technical solution of the present invention, the thiophene-phenothiazine compound or the pharmaceutically acceptable salt thereof, having the structural formula shown in the formula I, where $R_3$, $R_6$ and $R_7$, which are the same or different, are independently selected from hydrogen, halogen, hydroxyl groups, carboxyl groups, carbonyl groups, ester groups, cyano groups, nitro groups, amino groups, C1-C10 alkoxy groups, C1-C10 haloalkyl groups, C1-C10 alkyl groups, C1-C10 alkenyl groups, C1-C10 alkynyl groups, cyclic hydrocarbyl groups, or aryl groups, respectively.

As a preferred technical solution of the present invention, the thiophene-phenothiazine compound or the pharmaceutically acceptable salt thereof, having the structural formula shown in the formula I, where $R_3$, $R_6$ and $R_7$ which are the same or different are selected from hydrogen, halogen, hydroxyl groups, carboxyl groups, carbonyl groups, ester groups, cyano groups, nitro groups, methoxy groups, amino groups, fluoromethyl groups, methyl groups, ethyl groups, alkenyl groups, alkynyl groups, cyclic hydrocarbyl groups or aryl groups, respectively.

As a preferred technical solution of the present invention, the substituted substituents, which are the same or different, are independently selected from hydrogen, halogen, hydroxyl groups, carboxyl groups, carbonyl groups, cyano groups, nitro groups, amino groups, methyl groups, ethyl groups, propyl groups, methoxy groups, ethoxy groups, fluoromethyl groups, cyclopropyl groups, C1-C20 alkenyl groups, C1-C20 alkynyl groups, and C6-C20 aryl groups, respectively.

As a preferred technical solution of the present invention, one or more hydrogen atoms in $R_1$, $R_2$, $R_4$ and $R_5$ which are the same or different are substituted with halogen, hydroxyl groups, carboxyl groups, carbonyl groups, ester groups, cyano groups, nitro groups, methoxy groups, amino groups, fluoromethyl groups, methyl groups, ethyl groups, alkenyl groups, alkynyl groups, cyclic hydrocarbyl groups or aryl groups, respectively.

As a preferred technical solution of the present invention, the thiophene-phenothiazine compound or the pharmaceutically acceptable salt thereof, having a structure shown in a following formula II:

II

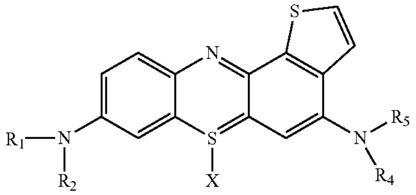

As a preferred technical solution of the present invention, the thiophene-phenothiazine compound or the pharmaceutically acceptable salt thereof, having one of structures shown below:

1-1

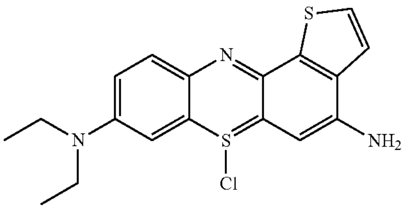

1-2

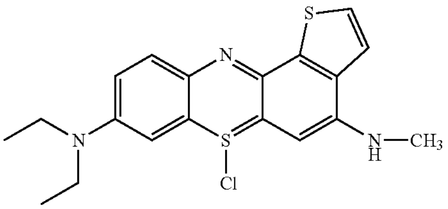

1-3

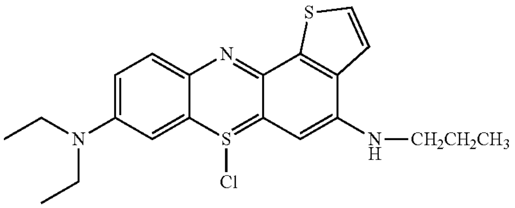

1-4

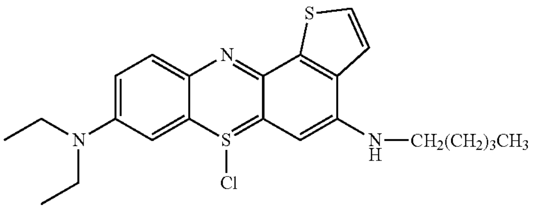

-continued 1-5

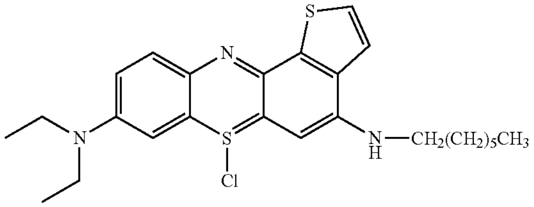

According to the thiophene-phenothiazine compound or the pharmaceutically acceptable salt thereof of the present invention, a thiophene structure is successfully fused to a phenothiazine framework, providing a novel molecular scaffold. The special structure exhibits excellent photodynamic activity, has strong wavelength absorption and good photostability in a near-infrared region, and can efficiently generate ROS under red light, and therefore, the thiophene-phenothiazine compound or the pharmaceutically acceptable salt thereof can be used as a photosensitizer.

The present invention also provides a preparation method of the thiophene-phenothiazine compound, including obtaining the thiophene-phenothiazine compound through a reaction of raw materials of an aniline analog (compound A) and a phenylpropanethiophene analog (compound B).

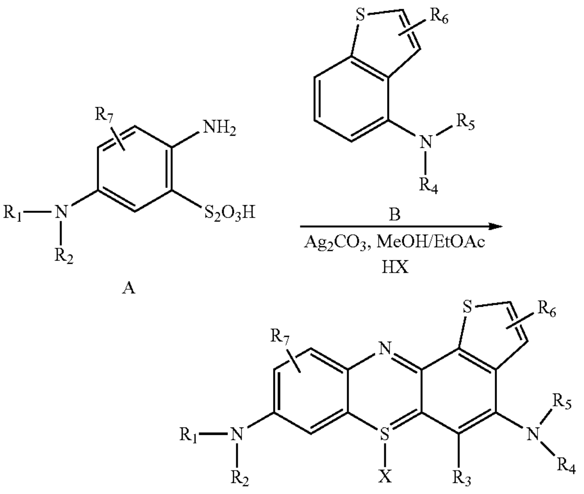

I

The aniline analog (compound A) can be directly purchased or prepared through conventional techniques in the art, such as referring to a preparation method of CN 107501297B, specifically referring to paragraph [0061].

The phenylpropathiophene analog (compound B) can be directly purchased or prepared using conventional techniques in the art through purchased materials, as shown in compounds B1 and B2.

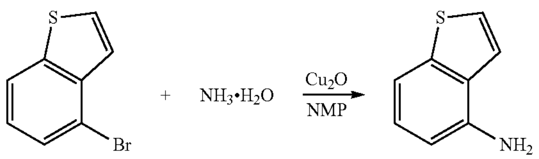

B1

-continued

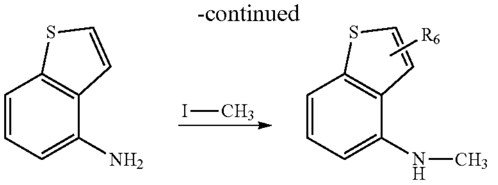

B1 B2

The present invention further provides a pharmaceutical composition, containing the thiophene-phenothiazine compound or the pharmaceutically acceptable salt thereof, and one or more pharmaceutically acceptable carriers or excipients.

Further, the excipient may include at least one of a diluent, a wetting agent, a lubricant, a filler and a preservative.

Further, the pharmaceutical composition is made into various pharmaceutical dosage forms by conventional methods, and the dosage forms include: tablets, capsules, oral liquid, oral lozenges, granules, pills, pellets, paste, suspensions, medicinal liquor, tinctures, cataplasm, drops, patches, smearing preparations, gel, sprays, aerosols, mucosal preparations and injections.

The present invention further provides application of the thiophene-phenothiazine compounds or the pharmaceutically acceptable salts thereof in preparation of phototherapy medicines or lead compounds thereof.

The thiophene-phenothiazine compound of the present invention has strong phototoxicity and high phototherapeutic indexes, exhibits strong photodynamic anti-tumor activity without obvious toxic and side effects, and is expected to become a new generation of clinically applicable novel photosensitizer for preparation of the phototherapy medicines or the lead compounds thereof.

Example 1: Synthesis of Thiophene-Phenothiazine Compound (Compound I-1)

(1) Synthesis of 2-amino-5-(diethylamino)-benzenesulfoperoxythioic O-acid (Compound A1)

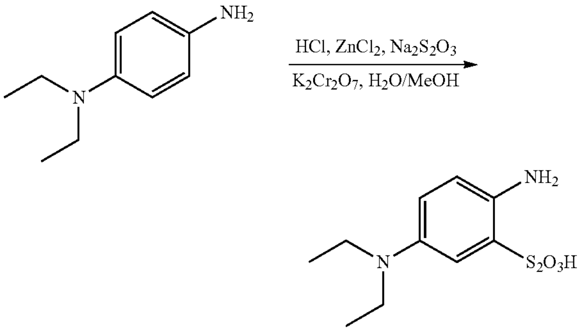

At room temperature, N,N-diethyl-p-phenylenediamine (1.0 g, 6 mmol), 0.6 mL of HCl (10 mol·$L^{-1}$), and 1 mL of a $ZnCl_2$ solution (6.3 mmol dissolved in water) were added to a mixed solution of water and methanol (12 mL, $H_2O$/MeOH 4:1). Then a reaction mixture was cooled in an ice bath to 0° C., and a newly prepared aqueous solution of sodium thiosulfate (3 mol·$L^{-1}$, 4 mL) and potassium dichromate (0.5 mol·$L^{-1}$, 3.6 mL) was added. After stirring at 0° C. for 3 hours, temperature was raised to room temperature, and stirring was continued for 1 hour to obtain a thick precipitation system; and filtration and separation were performed to obtain solid, the solid was washed with a solution of water, dichloromethane, ethyl acetate and methanol (>300 mL), and then drying was performed in a vacuum drying oven to obtain gray solid 2-amino-5-(diethylamino)-benzenesulfoperoxythioic O-acid (compound A1).

(2) Synthesis of 4-aminobenzo[b]thiophene (Compound B1)

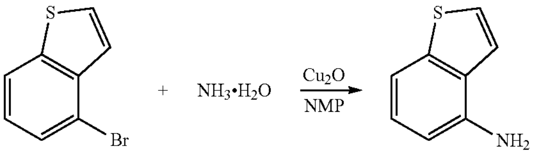

B1

4-bromobenzo[b]thiophene (2.74 g, 12.88 mmol) was added to a pressure bottle, and then $Cu_2O$(0.37 g, 2.60 mmol), 28 mL of an ammonia aqueous solution of 28-30% (w/w), and 28 mL of N-methylpyrrolidone (NMP) were added. A mixture was heated at 110° C. in an oil bath to react for 24 hours. Then, the mixture was cooled to room temperature, filtration was performed, 100 mL of cold water was added, and extraction was performed with ethyl acetate (100 mL×3 times). An organic solution was collected, and concentration by rotary evaporation was performed to 100 mL. Washing was performed with a large amount of a $NH_4Cl$ solution and saline water (100 mL×3 times) until a washing solution was colorless, and then a remaining organic solvent was spun off. The 4-aminobenzo[b]thiophene (compound B1) was obtained by purification through silica gel column chromatography, with a solvent mixture in which a ratio of n-hexane to dichloromethane was 1:1.

(3) Synthesis of the Thiophene-Phenothiazine Compound (Compound I-1)

The 2-amino-5-(diethylamino)-benzenesulfoperoxythioic O-acid (compound A1) (0.14 g, 0.5 mmol) and the 4-aminobenzo[b]thiophene (compound B1) (half of the molar quantity of compound A1) were stirred and refluxed in a mixed solution of methanol and ethyl acetate (6 mL, methanol/ethyl acetate=4:1), and silver carbonate (0.14 g, 0.5 mmol) was slowly added. After refluxing for 2 hours, a reaction mixture was cooled to room temperature, 2 g of diatomite was added, then filtration was performed, and filter residues were washed with methanol and dichloromethane alternatively. An organic solvent was collected, then the collected organic solvent was concentrated into blue solid, then the blue solid was dissolved in 5 mL of dichloromethane, and 0.25 mL of HCl (1 mol L-1, methanol) was added. A mixture was gently stirred and concentrated, and purifying was performed by using the silica gel column chromatography to obtain the compound I-1, with a solvent mixture in which a ratio of dichloromethane to methanol was 10:1.1H NMR (400 MHz, Methanol-$d_4$) δ7.84 (d, J=5.3 Hz, 1H), 7.76 (d, J=9.5 Hz, 1H), 7.71 (d, J=8.2 Hz, 1H), 7.34-7.25 (m, 1H), 7.14 (s, 1H), 6.90 (s, 1H), 3.67 (q, J=7.3 Hz, 4H), 1.38-1.28 (m, 6H). HRMS(ESI): calcd for $C_{18}H_{18}ClN_3S_2$ $[MCl]^+$340.09421; found, 340.09346.

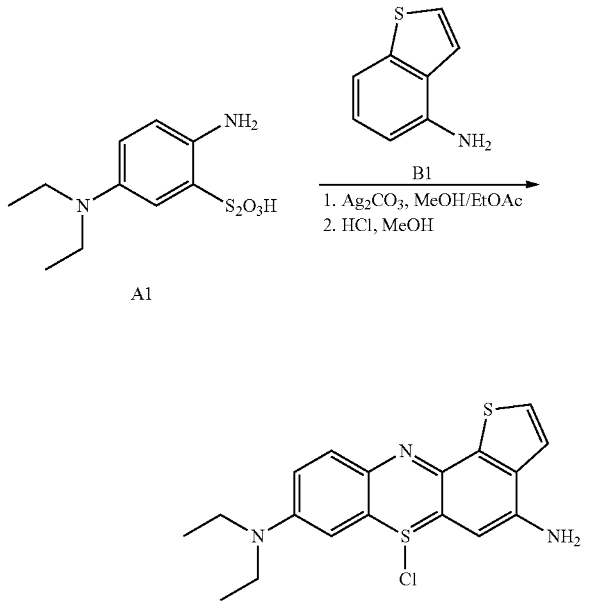

A1

I-1

Example 2: Synthesis of Thiophene-Phenothiazine Compound (Compound I-2)

(1) Synthesis of 2-Amino-5-(Diethylamino)-Benzenesulfoperoxythioic O-Acid (Compound A1) was the Same as that of Example 1

(2) Synthesis of N-methyl-4-aminobenzo[b]thiophene (Compound B2)

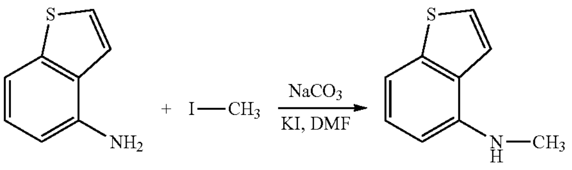

B1

B2

A compound B1 (0.6 g, 4 mmol), methyl iodide (0.74 mL, 12 mmol), sodium carbonate (0.53 g, 0.5 mmol), and potassium iodide (KI, 66.4 mg) were added to N, N-dimethylformamide (DMF, 10 mL), refluxing was performed at 60° C. for 24 hours, and after reaction mixed liquid was cooled to room temperature, 20 mL of water was added. Extraction was performed with ethyl acetate (20 mL×3 times), washing was performed with saturated $NH_4Cl$ and NaCl solutions, and drying was performed with $Na_2SO_4$. After reduced-pressure rotary evaporation was performed to remove the solvent, purifying was performed by using silica gel column chromatography (with a solvent mixture in which a ratio of n-hexane to ethyl acetate was 1:10) to obtain a light yellow oily substance, namely N-methyl-4-aminobenzo[b]thiophene (compound B2).

(3) Synthesis of the Thiophene-Phenothiazine Compound (Compound I-2)

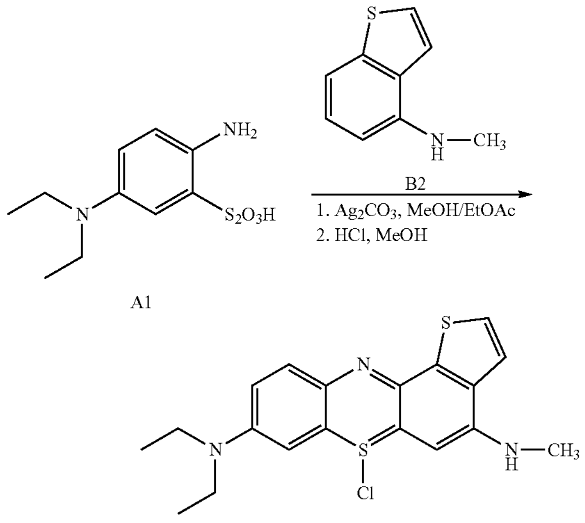

A1

I-2

Referring to the method in Example 1, the compound A1 was reacted with the compound B2 to prepare the thiophene-phenothiazine compound (Compound I-2). $^1H$ NMR (400 Mhz, Methanol-$d_4$) δ7.85 (d, J=5.4 Hz, 1H), 7.81 (d, J=9.5 Hz, 1H), 7.69 (d, J=5.4 Hz, 1H), 7.33 (dd, J=9.6, 2.5 Hz, 1H), 7.19 (d, J=2.6 Hz, 1H), 7.04 (s, 1H), 3.69 (q, J=7.2 Hz, 4H), 3.19 (s, 3H), 1.34 (t, J=6.4 Hz, 6H). HRMS(ESI): calcd for $C_{19}H_{20}ClN_3[M-Cl]^+$354.10986; found, 354.10897.

Example 3: Synthesis of Thiophene-Phenothiazine Compound (Compound I-3)

(1) Synthesis of 2-Amino-5-(Diethylamino)-Benzenesulfoperoxythioic O-Acid (Compound A1) was the Same as that of Example 1

(2) Synthesis of N-propyl-4-aminobenzo[b]thiophene (Compound B3)

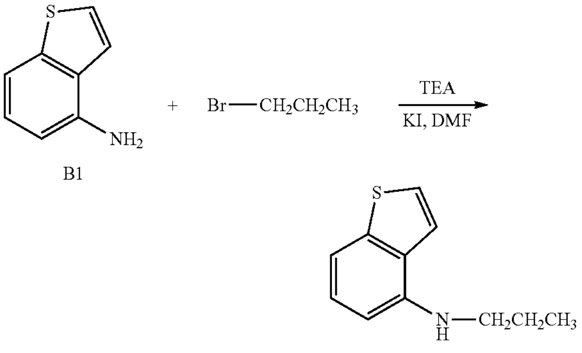

B1

B3

A compound B1 (0.6 g, 4 mmol), bromopropane (0.73 mL, 8 mmol), triethylamine (1.7 mL, 12 mmol), and potassium iodide (KI, 66.4 mg) were added to N, N-dimethylformamide (DMF, 10 mL), refluxing was performed at 70° C. for 48 hours, and after reaction mixed liquid was cooled to room temperature, 20 mL of water was added. Extraction was performed with ethyl acetate (20 mL×3 times), washing was performed with saturated $NH_4Cl$ and NaCl solutions, and drying was performed with $Na_2SO_4$. After reduced-pressure rotary evaporation was performed to remove a solvent, purifying was performed by using silica gel column chromatography (with a solvent mixture in which a ratio of n-hexane to ethyl acetate was 1:10) to obtain a light yellow oily substance, namely N-propyl-4-aminobenzo[b]thiophene (compound B3).

(3) Synthesis of the Thiophene-Phenothiazine Compound (Compound I-3)

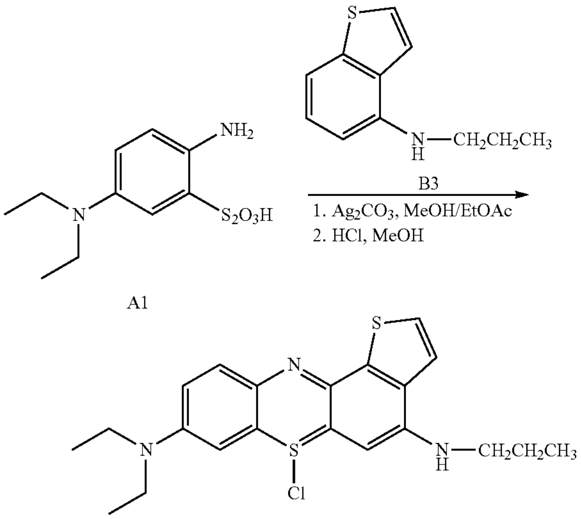

A1

I-3

Referring to the method in Example 1, the compound A1 was reacted with the compound B3 to prepare the thiophene-phenothiazine compound (Compound I-3). 1H NMR (400 MHz, Methanol-$d_4$) δ7.88-7.77 (m, 3H), 7.34 (dd, J=9.6, 2.6 Hz, 1H), 7.20 (d, J=2.6 Hz, 1H), 7.14 (s, 1H), 3.69 (q, J=7.5 Hz, 4H), 3.54 (t, J=7.4 Hz, 2H), 1.83 (p, J=7.5 Hz, 2H), 1.34 (t, J=7.1 Hz, 6H), 1.09 (t, J=7.4 Hz, 3H). HRMS(ESI): calcd for $C_{21}H_{24}ClN_3S_2$ $[M-Cl]^+$382.14116; found, 382.14007.

Example 4: Synthesis of Thiophene-Phenothiazine Compound (Compound I-4)

(1) Synthesis of 2-Amino-5-(Diethylamino)-Benzenesulfoperoxythioic O-Acid (Compound A1) was the Same as that of Example 1

(2) Synthesis of N-pentyl-4-aminobenzo[b]thiophene (Compound B4)

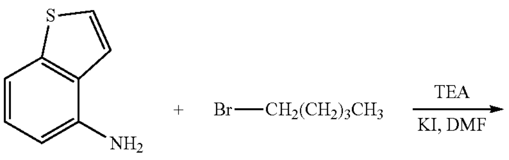

B1

-continued

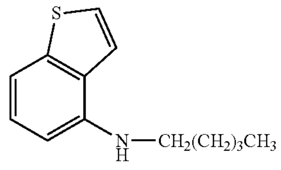

B4

The compound B1 (0.6 g, 4 mmol), bromopentane (1 mL, 8 mmol), triethylamine (1.7 mL, 12 mmol), and potassium iodide (KI, 66.4 mg) were added to N, N-dimethylformamide (DMF, 10 mL), refluxing was performed at 70° C. for 48 hours, then the mixed liquid was cooled to room temperature, 20 mL of water was added. Extraction was performed with ethyl acetate (20 mL×3 times), washing was performed with saturated $NH_4Cl$ and NaCl solutions, and drying was performed with $Na_2SO_4$. After reduced-pressure rotary evaporation was performed to remove a solvent, purifying was performed by using silica gel column chromatography (with a solvent mixture in which a ratio of n-hexane to ethyl acetate was 1:10) to obtain a light yellow oily substance, namely N-pentyl-4-aminobenzo[b]thiophene (compound B4).

(3) Synthesis of the Thiophene-Phenothiazine Compound (Compound I-4)

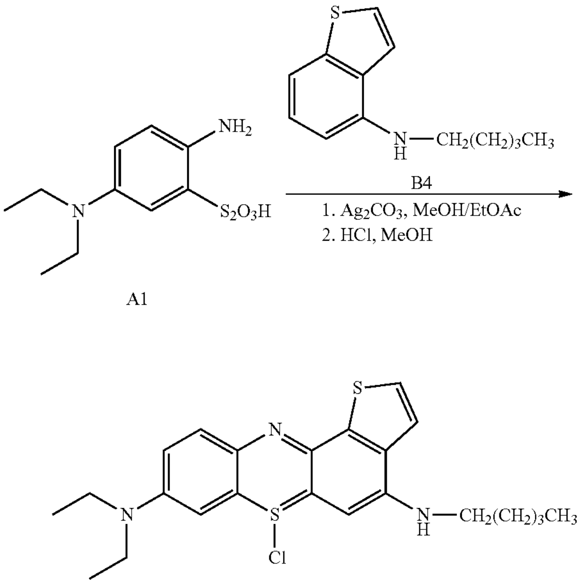

A1

I-4

Referring to the method in Example 1, the compound A1 was reacted with the compound B4 to prepare the thiophene-phenothiazine compound (Compound I-4). 1H NMR (400 MHz, Methanol-$d_4$) δ7.90-7.79 (m, 3H), 7.35 (dd, J=9.6, 2.6 Hz, 1H), 7.22 (d, J=2.6 Hz, 1H), 7.16 (s, 1H), 3.69 (q, J=7.2 Hz, 4H), 3.58 (t, J=7.4 Hz, 2H), 1.82 (p, J=7.8 Hz, 2H), 1.47 (dd, J=8.2, 4.5 Hz, 4H), 1.34 (t, J=7.1 Hz, 6H), 0.98 (t, J=7.0 Hz, 3H). HRMS(ESI): calcd for $C_{23}H_{28}ClN_3S_2$ $[MCl]^+$ 410.17246; found, 410.17151.

Example 5: Synthesis of Thiophene-Phenothiazine Compound (Compound I-5)

(1) Synthesis of 2-Amino-5-(Diethylamino)-Benzenesulfoperoxythioic O-Acid (Compound A1) was the Same as that of Example 1

(2) Synthesis of N-heptyl-4-aminobenzo[b]thiophene (Compound B5)

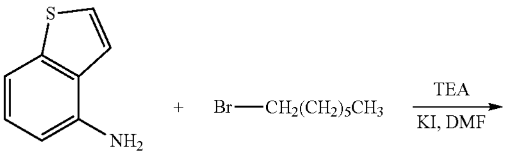

B1

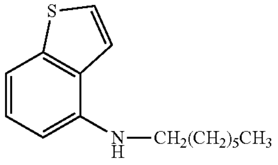

B5

The compound B1 (0.6 g, 4 mmol), bromoheptane (1.26 mL, 8 mmol), triethylamine (1.7 mL, 12 mmol), and potassium iodide (KI, 66.4 mg) were added to N, N-dimethylformamide (DMF, 10 mL), refluxing was performed at 70° C. for 48 hours, and then the mixed liquid was cooled to room temperature, 20 mL of water was added. Extraction was performed with ethyl acetate (20 mL×3 times), washing was performed with saturated $NH_4Cl$ and NaCl solutions, and drying was performed with $Na_2SO_4$. After reduced-pressure rotary evaporation was performed to remove a solvent, purifying was performed by using silica gel column chromatography (with a solvent mixture in which a ratio of n-hexane to ethyl acetate was 1:10) to obtain a light yellow oily substance, namely N-heptyl-4-aminobenzo[b]thiophene (compound B5).

(3) Synthesis of the Thiophene-Phenothiazine Compound (Compound I-5)

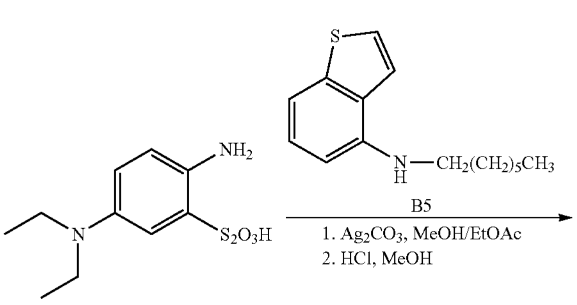

A1

-continued

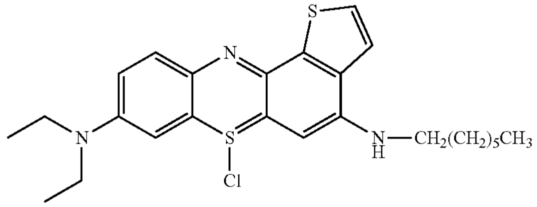

I-5

Referring to the method in Example 1, the compound A1 was reacted with the compound B5 to prepare the thiophene-phenothiazine compound (Compound I-5). 1H NMR (400 Mhz, Methanol-$d_4$) δ7.88-7.77 (m, 3H), 7.34 (dd, J=9.7, 2.2 Hz, 1H), 7.20 (d, J=2.2 Hz, 1H), 7.14 (s, 1H), 3.69 (q, J=7.7, 6.9 Hz, 4H), 3.57 (t, J=7.4 Hz, 2H), 1.81 (p, J=7.8, 7.3 Hz, 2H), 1.54-1.40 (m, 4H), 1.33 (t, J=7.0 Hz, 10H), 0.92 (t, J=6.5 Hz, 3H). HRMS(ESI): calcd for $C_{25}H_{32}ClN_3[MCl]^+$ 438.20376; found, 438.20283.

Example 6: Physiological and Chemical Properties of Thiophene-Phenothiazine Compound (1) Absorption Spectrum and Emission Spectrum Detection of the thiophene-phenothiazine compounds prepared in Examples 1-5: the absorption spectrum of the thiophene-phenothiazine compound in an ethanol solution was measured by using a UV-visible spectrophotometer, and spectral properties of the thiophene-phenothiazine compound were analyzed according to Beer-Lambert law; and a fluorescence emission spectrum of the thiophene-phenothiazine compound in the ethanol solution was measured under excitation of light with a wavelength of 650 nm, and results are shown in Table 1 and FIGS. 2-3.

Figure 2:
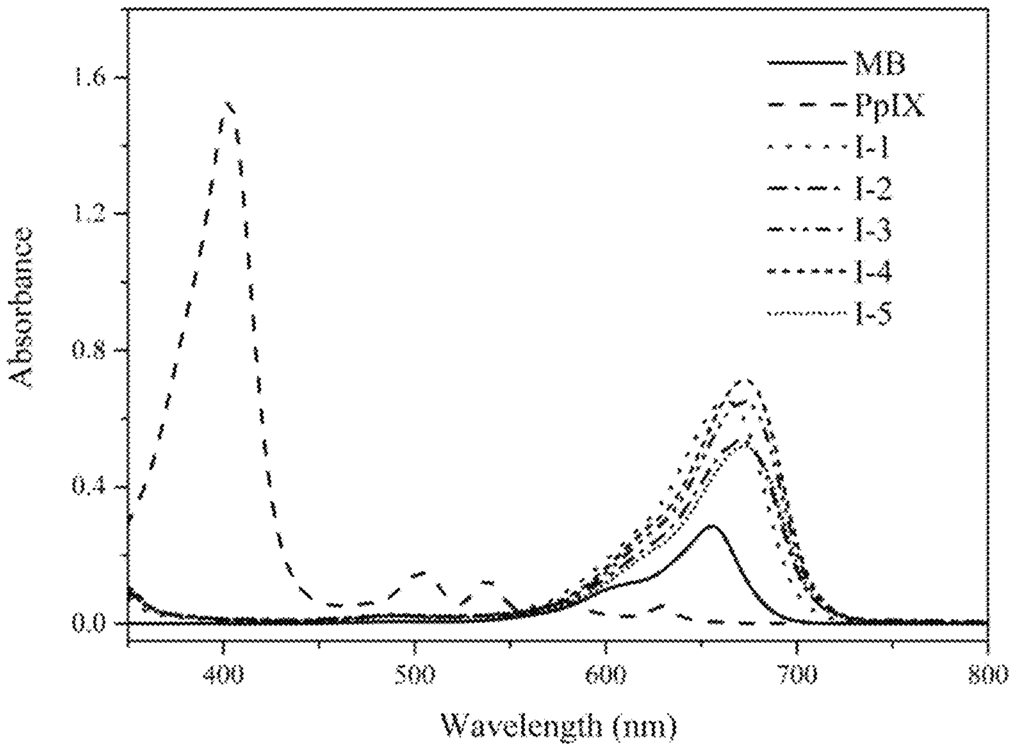
FIG. 2 shows absorption spectra of thiophene-phenothiazine compounds of the present invention, where MB is methylene blue, PpIX is protoporphyrin IX, and concentrations are all 2 μM.

As shown in FIG. 2, an absorption value of the thiophene-phenothiazine compound of the present invention follows Lambert-Beer law, indicating that the thiophene-phenothiazine compound of the present invention is stable and not prone to aggregation. The maximum absorption wavelengths of the thiophene-phenothiazine compounds are all greater than 660 nm, and the maximum effective absorption wavelengths are greater than 700 nm, which are greater than those of PpIX and MB, indicating that the compound of the present invention uses a longer-wavelength light source with better penetration for PDT, which is beneficial for treatment of deeper lesions.

Strong absorbance is a key factor in promoting efficient generation of ROS. Molar extinction coefficients of the compounds of the present invention are all greater than $10^6$ $mol^{-1}$ $cm^{-1}$, which are significantly improved compared with those of porphyrin compounds (3000-5000 $mol^{-1}$ $cm^{-1}$). Extinction coefficients of the compounds of the present invention also have significant advantages compared with other photosensitizers such as PpIX and photofrin. Compared with porphyrin-based photosensitizers, no absorption is observed in the range of 350-450 nm for the thiophene-phenothiazine compounds of the present invention, greatly reducing background interference from tissue (such as heme) and reducing skin phototoxicity caused by sunlight.

Figure 3:
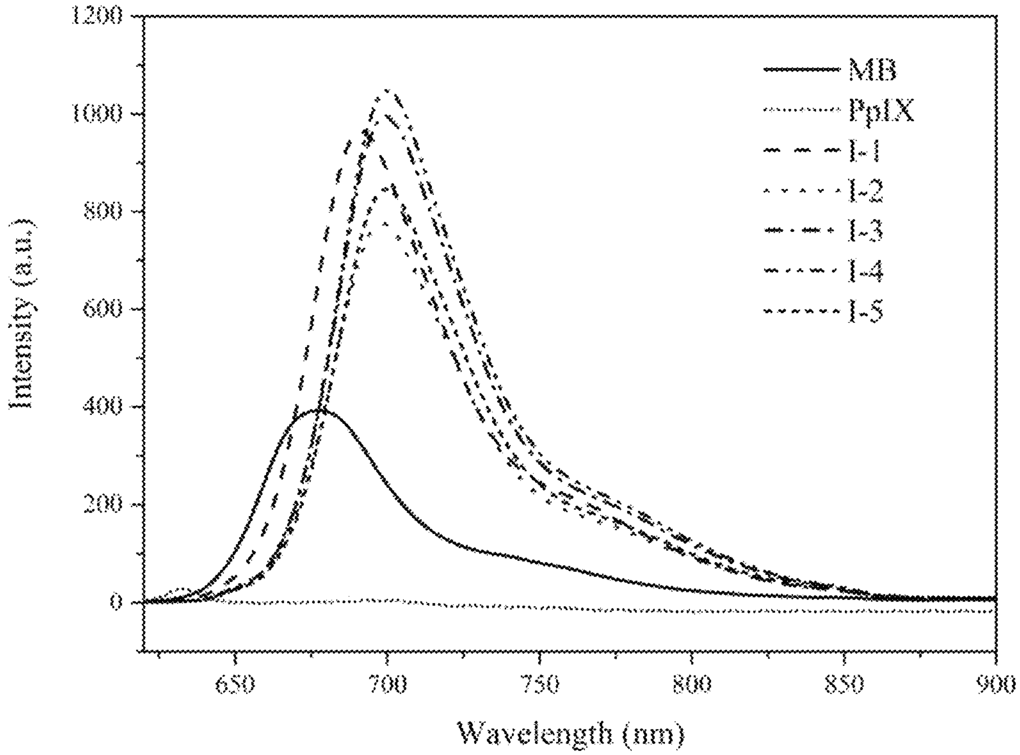
FIG. 3 shows fluorescence emission spectra of the thiophene-phenothiazine compounds of the present invention, where MB is methylene blue, PpIX is protoporphyrin IX, concentrations are all 2 μM, and wavelength of excitation light is 650 nm.

As shown in FIG. 3, the maximum fluorescence emission wavelengths of the thiophene-phenothiazine compounds of the present invention are greater than 800 nm, fluorescence intensities at the maximum emission wavelengths are much greater than those of MB and PpIX, and fluorescence quantum yields are greater than that of MB ($\phi_F$=0.04), indicating that the compounds of the present invention have strong fluorescence generation capability and superior fluorescence imaging potential.

TABLE 1

| Compound | $\lambda_{max}$[nm][a] | $\varepsilon[10^6 mol^{-1} \cdot cm^{-1}]$ | $\lambda_{em}$[nm][b] | $\phi_F^c$ |
|---|---|---|---|---|
| I-1 | 663 | 6.51 | 692 | 0.4 |
| I-2 | 671 | 5.35 | 698 | 0.5 |
| I-3 | 673 | 6.5 | 700 | 0.6 |
| I-4 | 673 | 7.13 | 701 | 0.5 |
| I-5 | 674 | 5.19 | 700 | 0.6 |

a. Absorbance was measured in ethanol.

b. During fluorescence emission spectrum measurement, an excitation wavelength was 650 nm, and a solvent was methanol.

c. $\phi_F$ of MB was used as a reference [$\phi_F$=0.04, methanol].

(2) Photostability

Good photostability is a prerequisite for ensuring continuous generation of ROS by the photosensitizers under light excitation, which can effectively prevent decomposition of the photosensitizers after illumination, avoiding a decrease in a ROS generation rate with increasing illumination time. An LED light source (630 nm, 106 mW $cm^{-2}$) was used to continuously irradiate the compound (5 μM), and a UV-visible spectrophotometer was used to measure the absorption spectrum of the compound at 200-800 nm. The photostability of the compound was evaluated by comparing changes in maximum absorption values at 600-800 nm after different irradiation times.

Figure 4:
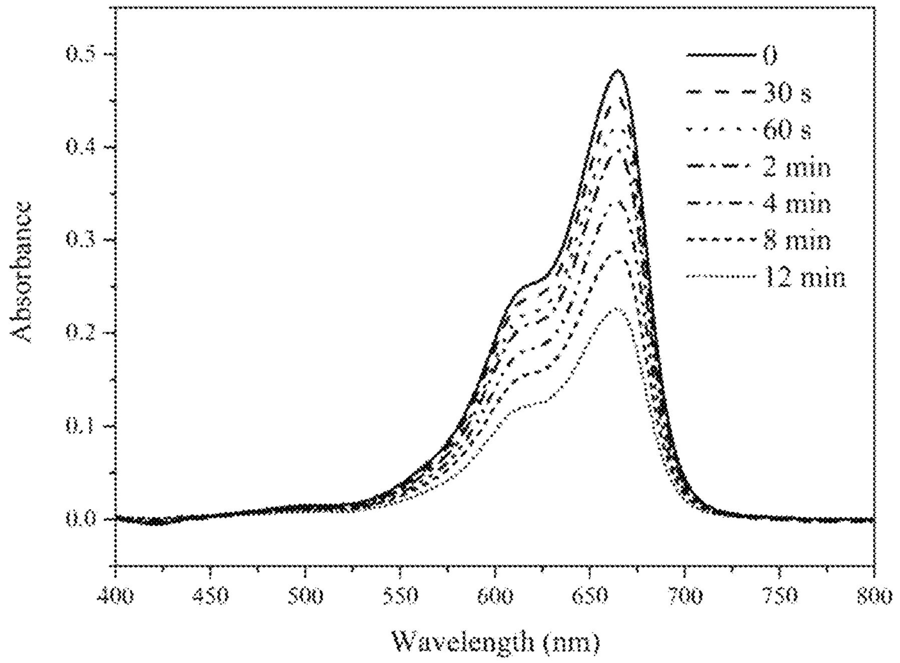
FIG. 4 shows a photolysis diagram of the thiophene-phenothiazine compound of the present invention, where (1) is MB, (2) is compound I-3 of the present invention, concentrations are all 2 μM, and wavelength of excitation light is 630 nm.
Figure 4:
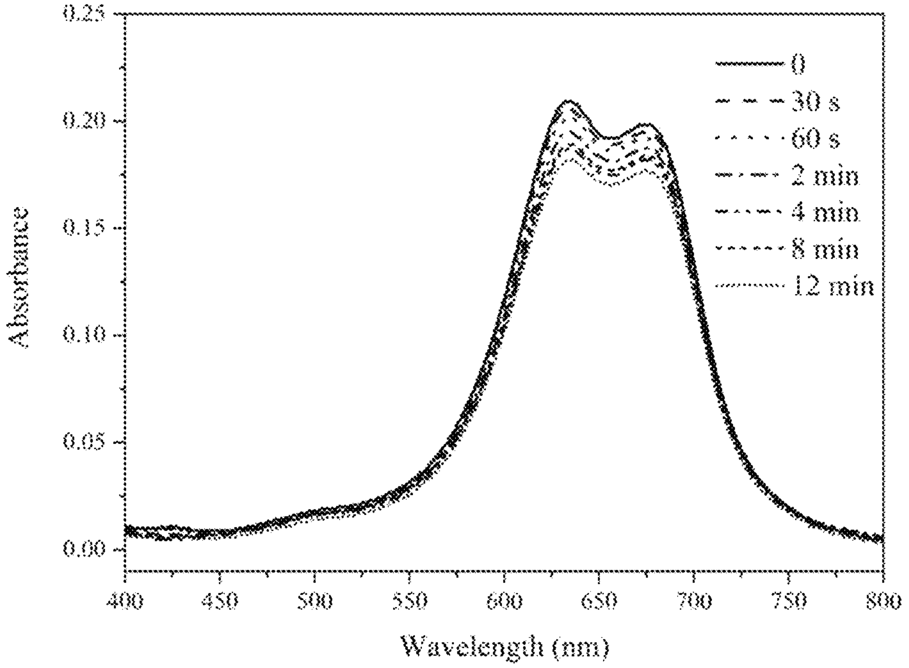

FIG. 4 shows a photolysis diagram of a thiophene-phenothiazine compound of the present invention, where the concentrations are 2 μM, wavelength of excitation light is 630 nm, (1) is MB, and (2) is the compound I-3 of the present invention. Result diagrams of other compounds are similar to that of the compound I-3. As can be seen from this figure, the maximum absorption value of the thiophene-phenothiazine compound of the present invention does not show a significant change as irradiation time increases, indicating that the thiophene-phenothiazine compound has significantly better photostability compared with MB. This is because a thiophene structure is introduced into the structure of the thiophene-phenothiazine compound of the present invention, which can significantly reduce a photolysis rate of a phenothiazine compound and enhance the photostability of the phenothiazine compound.

Example 7: Biological Activity of Thiophene-Phenothiazine Compound (1)Cell culture: HUVEC cells (human umbilical vein endothelial cells), A549 cells (human lung cancer cells), MCF-7 cells (human breast cancer cells), Hela cells (human cervical cancer cells) and 4T1 cells (mouse breast cancer cells) were cultured in a DMEM high-glucose medium containing 10% fetal bovine serum and 1% penicillin-streptomycin at 37° C. and under a condition of a 5% carbon dioxide content. The HUVEC cells, the A549 cells, the MCF-7 cells, the Hela cells and the 4T1 cells, at a logarithmic growth phase, were taken and inoculated into a 96-well plate, respectively, with approximately $1\times10^4$ cells per well, and incubation was performed overnight at 37° C. and under a condition of 5% $CO_2$.

(2) Dark toxicity measurement: the cells were incubated in a dark environment with the compound of the present invention of different concentrations for 24 hours, and cell viability was measured by a CCK-8 method.

(3) Phototoxicity measurement: the cells were incubated in the dark with the compound of the present invention of different concentrations for 1 hour, rinsing was performed with PBS, a fresh culture solution was added, and the cells were irradiated with 630 nm LED light (light dose is 3.2 J cm-2). Then the cells were incubated in the dark environment for 24 hours, and cell viability was measured by the CCK-8 method.

Figure 5:
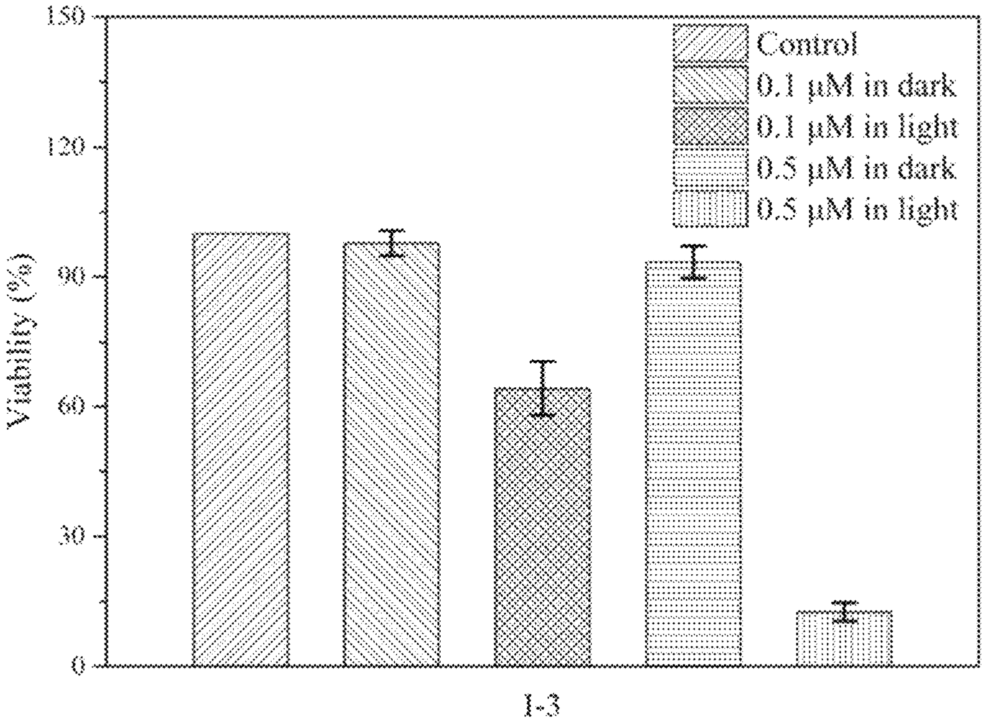
FIG. 5 shows results of a cell toxicity test of the thiophene-phenothiazine compound of the present invention.
Figure 6:
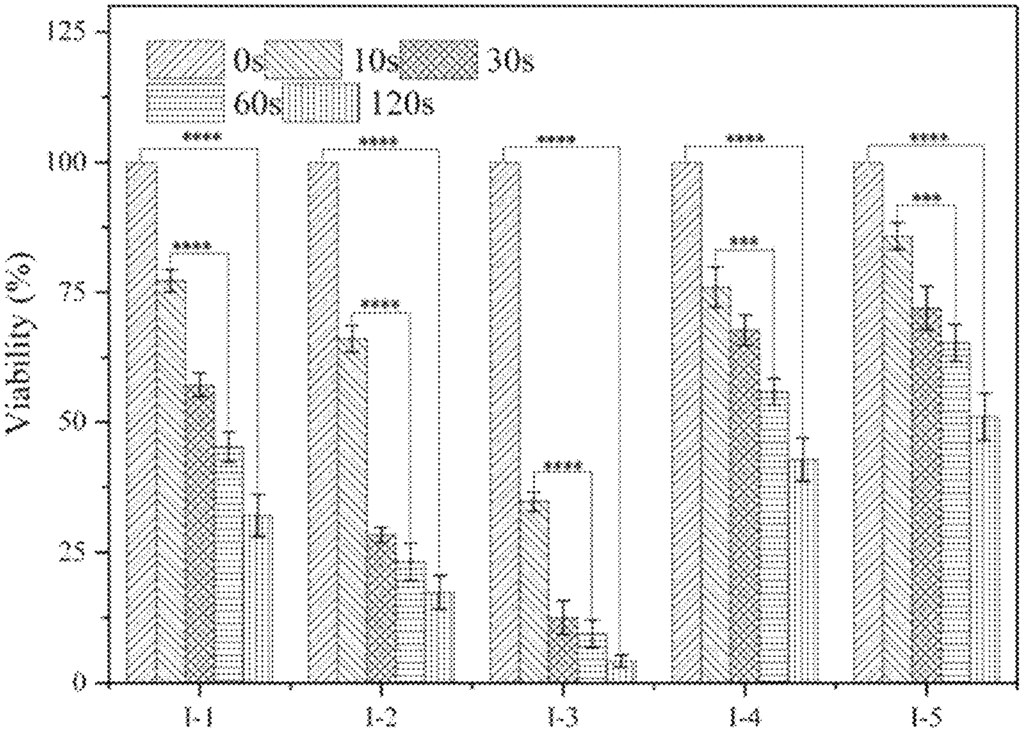
FIG. 6 shows results of cell phototoxicity tests of the thiophene-phenothiazine compounds of the present invention.

Test results are shown in Table 2-Table 3 and FIG. 5-FIG. 6.

TABLE 2

Phototoxicity and dark toxicity of thiophene-phenothiazine compounds in tumor cells $IC_{50}$ (μM)

| | MCF-7 | | | A549 | | | 4T1 | | | HeLa | | |
|---|---|---|---|---|---|---|---|---|---|---|---|---|
| | PDK | DK | PI | PDK | DK | PI | PDK | DK | PI | PDK | DK | PI |
| I-1 | 0.39 | 3.56 | 9.03 | 0.46 | 7.54 | 16.47 | 0.87 | 15.43 | 17.69 | 0.36 | 3.74 | 10.26 |
| I-2 | 0.14 | 2.03 | 14.2 | 0.32 | 6.93 | 21.66 | 0.40 | 9.79 | 24.41 | 0.13 | 3.14 | 23.49 |
| I-3 | 0.12 | 2.86 | 24.00 | 0.21 | 6.59 | 31.35 | 0.19 | 8.67 | 44.51 | 0.07 | 2.40 | 32.72 |
| I-4 | 0.39 | 3.49 | 9.05 | 0.31 | 3.49 | 11.09 | 1.32 | 5.48 | 4.16 | 0.44 | 1.89 | 4.32 |
| I-5 | 0.47 | 3.34 | 7.11 | 0.42 | 3.57 | 8.57 | 1.92 | 4.27 | 2.22 | 0.43 | 1.44 | 3.32 |
| MB | * | * | * | * | * | * | 14.13 | 25.67 | 1.82 | * | * | * |

TABLE 3

Dark toxicity of thiophene-phenothiazine compounds in HUVEC cells

| Compound | $IC_{50}$ (μM) |
|---|---|
| I-1 | 25.15 |
| I-2 | 17.55 |
| I-3 | 13.59 |
| I-4 | 10.41 |
| I-5 | 7.63 |

From FIG. 5-FIG. 6, it can be seen that the cytotoxicities of the thiophene-phenothiazine compounds of the present invention under illumination are significantly higher than those under a dark condition, and these thiophene-phenothiazine compounds exhibited good illumination time dependence, confirming that the thiophene-phenothiazine compounds have good light controlled cytotoxicity reaction.

This is also one of advantages of PDT, which can achieve phototoxicity required for treatment by prolonging the illumination time.

As shown in Tables 2-3, the thiophene-phenothiazine compound of the present invention had excellent photodynamic activity. Where a ratio of the phototoxicity to the dark toxicity is a phototherapeutic index (PI), and the higher the phototherapeutic index, the higher a safety threshold of the photosensitizer; in 4T1 cells, the phototoxicity of the compound of the present invention can reach 74.35 times that of MB by comparing an $IC_{50}$ value of the compound with that of MB, while a PI value of the compound can reach 24.46 times that of MB. Therefore, the compound of the present invention has a significantly enhanced therapeutic effect compared with MB.

In the HUVEC cells, the dark toxicity $IC_{50}$ value of the thiophene-phenothiazine compound of the present invention is lower than that in tumor cells, indicating that the thiophene-phenothiazine compound of the present invention has higher selectivity for the tumor cells.

Example 8: Photosensitive Efficiency of Thiophene-Phenothiazine Compound

Figure 7:
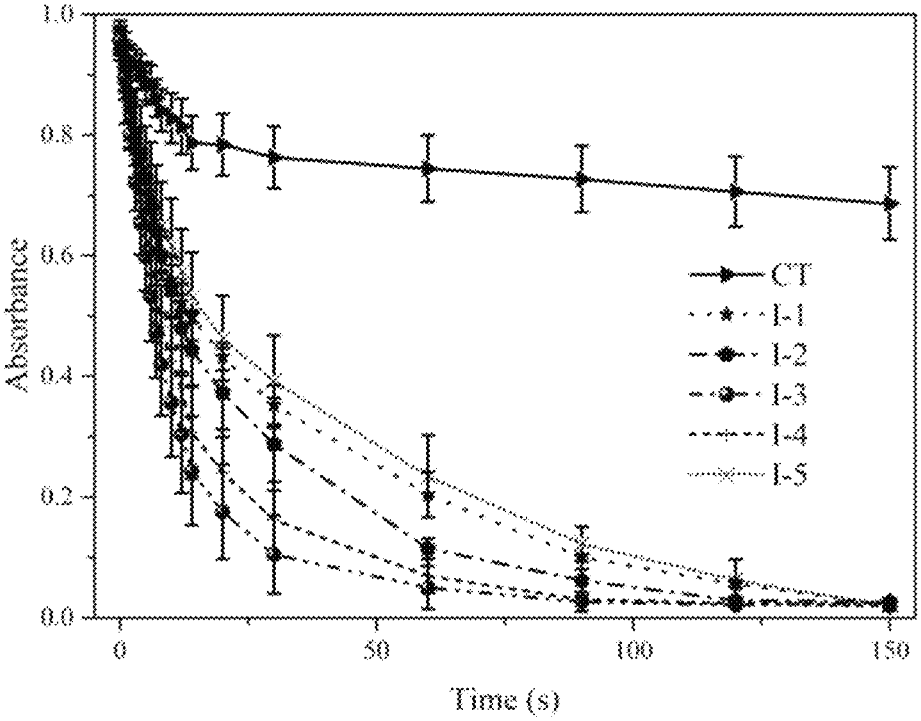
FIG. 7 shows singlet oxygen generation curves of the thiophene-phenothiazine compounds of the present invention, where concentrations are all 2 μM, and wavelength of excitation light is 630 nm.

The efficiency of producing singlet oxygen through photosensitization is an important index for evaluating the photosensitizers. In the example, a conventional steady-state method was used, 1,3-diphenylisobenzofuran (DPBF) was used as a scavenger, which irreversibly reacted with the singlet oxygen to cause attenuation of the DPBF. An attenuation rate of the DPBF reflects production efficiency of $^1O_2$. Concentrations of the DPBF in EtOH at multiple irradiation time periods were measured by using a UV/Vis spectrum method. A medicine solution (2 μM in EtOH) was irradiated with a 630 nm LED lamp (106 $Mw/cm^2$), and results were shown in FIG. 7. As can be seen from the figure, the thiophene-phenothiazine compounds of the present invention rapidly and effectively generate $^1O_2$ under light irradiation conditions, where compound I-3 can achieve 80% photosensitive efficiency under irradiation for 20 s.

Figure 8:
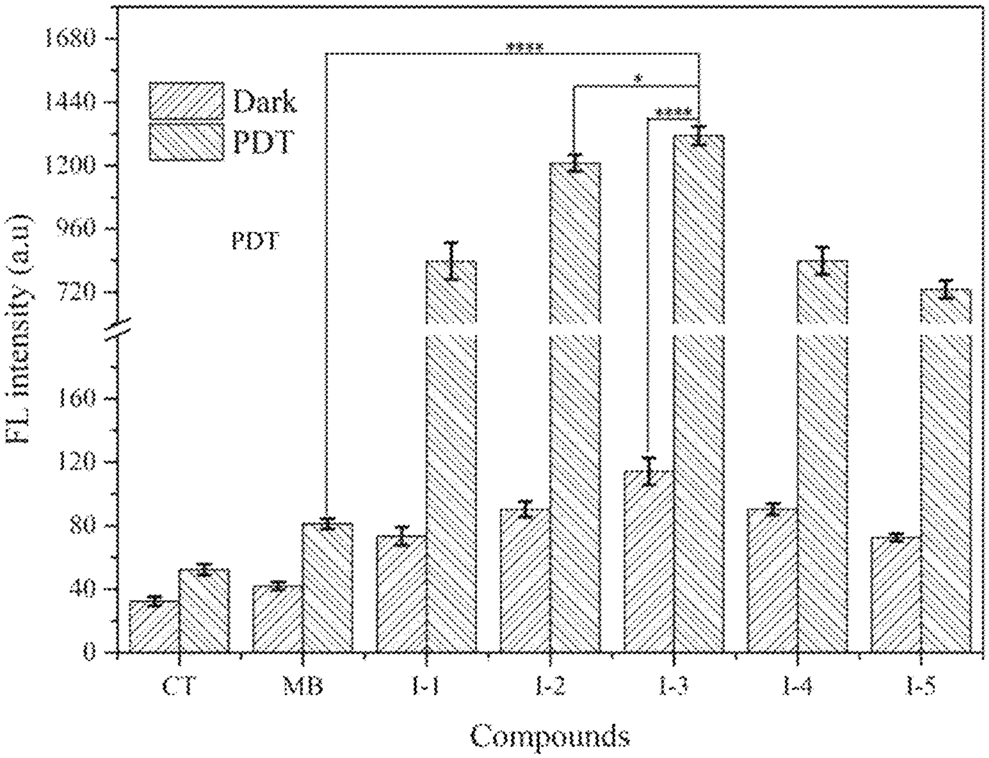
FIG. 8 shows intracellular reactive oxygen species levels of the thiophene-phenothiazine compounds of the present invention, where the concentration is 0.5 μM.

Dichlorodihydrofluorescein diacetate (DCFH-DA) was used as a scavenger, production of intracellular ROS was detected by a flow cytometer to detect the production efficiency of intracellular reactive oxygen species (ROS) of the thiophene-phenothiazine compounds of the present invention. The results were shown in FIG. 8. As shown in the figure, compared with MB, the thiophene-phenothiazine compounds of the present invention exhibit a significantly increased ROS level at a concentration of 0.5 μM under light irradiation in cells, up to 16 times the ROS level of MB.

Example 9: Tumor Inhibitory Effects of Thiophene-Phenothiazine Compound in Mice 7-week-old BALB/c female mice weighing 18 g±1 g (purchased from Zhejiang Vital River Laboratory Animal Technology Co., Ltd) were used to construct a subcutaneous breast cancer (4T1) tumor model. When tumor volumes of the BALB/c mice were approximately 100 $mm^3$, in vivo anti-tumor experiments began. When the tumor volumes of the BALB/c mice were approximately 200 $mm^3$, imaging experiments began.

Figure 9:
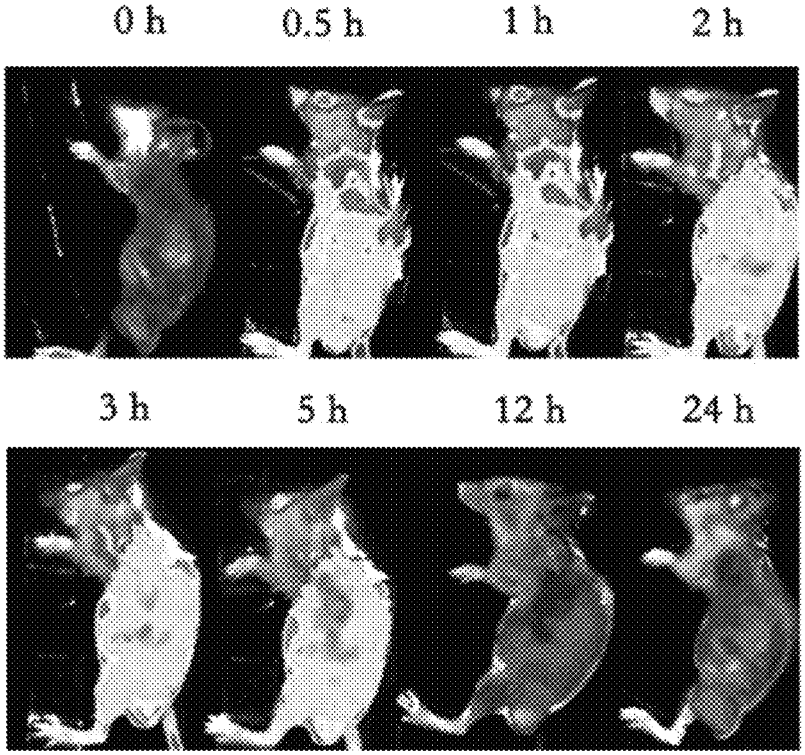
FIG. 9 shows distribution of the thiophene-phenothiazine compound of the present invention in BALB/c tumor bearing mice at different times.

(1) Distribution Detection of the Thiophene-Phenothiazine Compound in 4T1 Subcutaneous Tumors of the Mice A solution of 10 mg/L was prepared from the compound I-3 of the present invention by using 1×PBS. The BALB/c mice with the tumor volumes of approximately 200 $mm^3$ were taken, and the solution was injected into tumor bearing mice via tail veins at a dose of 1.6 mg/kg. Imaging photos were taken at different times using Odyssey CLX, with excitation light of 680 nm and detection light of 720 nm. The results were shown in FIG. 9. As can be seen from the figure, the thiophene-phenothiazine compound of the present invention can gradually accumulate in tumors after 1 hour, reached its maximum accumulation in the tumors after 2 hours, and was basically not detected after 24 hours. It indicates that the thiophene-phenothiazine compound of the present invention can be metabolized in mice within 24 hours. Because long-time accumulation of the photosensitizers in bodies was a major obstacle to clinical application of PDT, for example, porfimer sodium has a metabolic time of about ten weeks in the bodies, which easily causes skin phototoxicity. Therefore, the thiophene-phenothiazine compound of the present invention can be completely metabolized within 24 hours, effectively solving a metabolic problem in existing PDT treatment mentioned above.

Figure 10:
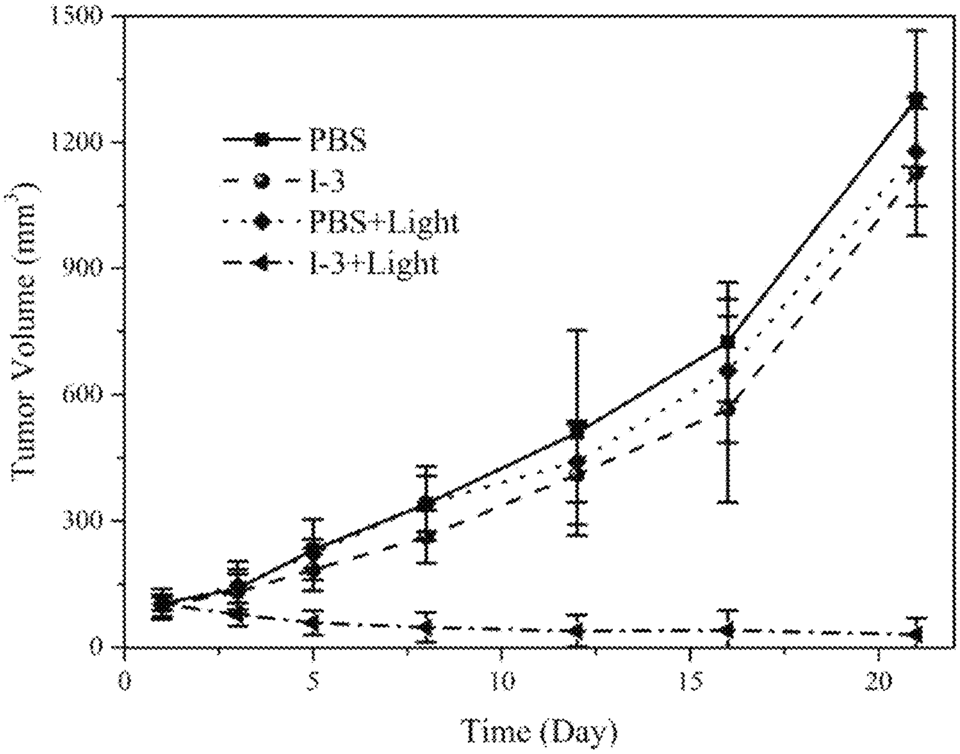
FIG. 10 shows a change curve of tumor volumes in the BALB/c mice after PDT.

(2) In Vivo Experiments of the Thiophene-Phenothiazine Compound Inhibit the Growth of Breast Cancer The BALB/c mice with the tumor volumes of approximately 100 $mm^3$ were taken, and the tumor bearing mice were divided into 4 groups, namely groups A, B, C and D, with 5 mice in each group. The mice in the group A and the group B were injected with 1×PBS 100 μL via tail veins. In addition, the mice in the group C and the group D were injected with compound I-3 via the tail veins at a dose of 1.6 mg/kg; and after 2 hours, the mice in the group B and the group D were irradiated with a light source (655 nm, 300 $mW\,cm^{-2}$) for 10 minutes. Body weights and tumor volumes of the mice were measured on the 2nd day, 4th day, 8th day, 12th day, 16th day, and 21st day, respectively. On the 21st day, approximately 0.8 mL of mouse blood was collected using an eyeball blood sampling method, of which 0.4 mL of the mouse blood was placed in an EDTA-2K anticoagulant tube, and the remaining 0.4 mL of the mouse blood was centrifuged for serum collection. FIG. 10 shows a change curve of tumor volumes in the BALB/c mice after PDT.

As shown in the figure, compared with those in the group A (PBS), the group B (PBS+irradiation), and the group C(Compound I-3 alone), growth of tumor volumes in the group D (Compound I-3+light irradiation) was significantly inhibited, and the tumor volumes in the mice showed a gradually decreasing trend, while the group of the compound I-3 alone did not show tumor growth inhibition. Therefore, the thiophene-phenothiazine compound of the present invention exhibits enormous potential for photodynamic tumor therapy.

Detection of body weight was performed on the tumor bearing mice in four groups within 21 days, and all results showed a similar increasing trend, indicating that the biological toxicity of the thiophene-phenothiazine compound of the present invention is relatively low. After 21 days of various treatments, blood biochemical analysis was performed on the mice. No significant abnormalities were found in serum, alanine aminotransferase (ALT), blood urea nitrogen (BUN), aspartate aminotransferase (AST), and uric acid (UA) of the mice, and liver and kidney function damage was not significant. Besides, through H&E staining analysis of main organs, normal cell morphology was shown between different groups, indicating that there was no significant toxic damage to internal tissue of the mice. Therefore, the thiophene-phenothiazine compound of the present invention has achieved the effect of successfully inhibiting tumor growth with ultra-low side effects.

The above examples are preferred implementations of the present invention. However, the implementations of the present invention are not limited by the above examples. Any change, modification, replacement combination, and simplification made without departing from the spiritual essence and principle of the present invention should be an equivalent replacement manner, and all are included in the protection scope of the present invention.

What is claimed is:

1. A compound of formula I:

I

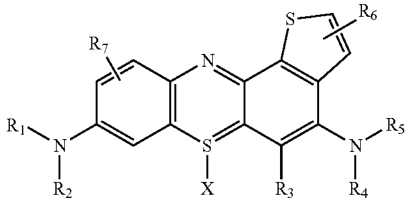

or a pharmaceutically acceptable salt thereof, wherein:

$R_1$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O) alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, O(alkyl), cycloalkyl, cycloalkenyl, cycloalkynyl, and aryl; and wherein the phenyl of benzyl, C(O)cycloalkyl, C(O) heterocyclyl, C(O)aryl, C(O)heteroaryl, $Si(phenyl)_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, alkyl, haloalkyl, alkenyl, alkynyl, C(O)H, C(O) alkyl, C(O)alkenyl, C(O)alkynyl, C(O)OH, C(O) Oalkyl, C(O)cycloalkyl, C(O)heterocyclyl, C(O) aryl, C(O)heteroaryl, $NH_2$, OH, O(alkyl), cycloalkyl, cycloalkenyl, cycloalkynyl, and aryl;

$R_2$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O) alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, O(alkyl), cycloalkyl, cycloalkenyl, cycloalkynyl, and aryl; and wherein the phenyl of benzyl, C(O)cycloalkyl, C(O) heterocyclyl, C(O)aryl, C(O)heteroaryl, $Si(phenyl)_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, alkyl, haloalkyl, alkenyl, alkynyl, C(O)H, C(O) alkyl, C(O)alkenyl, C(O)alkynyl, C(O)OH, C(O) Oalkyl, C(O)cycloalkyl, C(O)heterocyclyl, C(O) aryl, C(O)heteroaryl, $NH_2$, OH, O(alkyl), cycloalkyl, cycloalkenyl, cycloalkynyl, and aryl; or $R_1$ and $R_2$, taken together with the nitrogen atom to which they are attached, form a heterocyclyl or heteroaryl, wherein the heterocyclyl or heteroaryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O) OH, C(O)Oalkyl, C(O)cycloalkyl, C(O)heterocyclyl, C(O)aryl, C(O)heteroaryl, $NH_2$, OH, O(alkyl), cycloalkyl, cycloalkenyl, cycloalkynyl, and aryl;

$R_7$ is H, halogen, CN, $NO_2$, alkyl, haloalkyl, alkenyl, alkynyl, C(O)H, C(O)alkyl, C(O)alkenyl, C(O)alkynyl, C(O)OH, C(O)Oalkyl, C(O)cycloalkyl, C(O) heterocyclyl, C(O)aryl, C(O)heteroaryl, $NH_2$, OH, O(alkyl), cycloalkyl, cycloalkenyl, cycloalkynyl, or aryl;

X is halogen;

$R_6$ is H, halogen, CN, $NO_2$, alkyl, haloalkyl, alkenyl, alkynyl, C(O)H, C(O)alkyl, C(O)alkenyl, C(O)alkynyl, C(O)OH, C(O)Oalkyl, C(O)cycloalkyl, C(O) heterocyclyl, C(O)aryl, C(O)heteroaryl, $NH_2$, OH, O(alkyl), cycloalkyl, cycloalkenyl, cycloalkynyl, or aryl;

$R_3$ is H, halogen, CN, $NO_2$, alkyl, haloalkyl, alkenyl, alkynyl, C(O)H, C(O)alkyl, C(O)alkenyl, C(O)alkynyl, C(O)OH, C(O)Oalkyl, C(O)cycloalkyl, C(O) heterocyclyl, C(O)aryl, C(O)heteroaryl, $NH_2$, OH, O(alkyl), cycloalkyl, cycloalkenyl, cycloalkynyl, or aryl;

$R_4$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O) alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, O(alkyl), cycloalkyl, cycloalkenyl, cycloalkynyl, and aryl; and wherein the phenyl of benzyl, C(O)cycloalkyl, C(O) heterocyclyl, C(O)aryl, C(O)heteroaryl, Si(phenyl)$_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, alkyl, haloalkyl, alkenyl, alkynyl, C(O)H, C(O) alkyl, C(O)alkenyl, C(O)alkynyl, C(O)OH, C(O) Oalkyl, C(O)cycloalkyl, C(O)heterocyclyl, C(O) aryl, C(O)heteroaryl, $NH_2$, OH, O(alkyl), cycloalkyl, cycloalkenyl, cycloalkynyl, and aryl; and $R_5$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, Si(alkyl)$_3$, Si(phenyl)$_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O) alkynyl, Si(alkyl)$_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, O(alkyl), cycloalkyl, cycloalkenyl, cycloalkynyl, and aryl; and wherein the phenyl of benzyl, C(O)cycloalkyl, C(O) heterocyclyl, C(O)aryl, C(O)heteroaryl, Si(phenyl)$_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, alkyl, haloalkyl, alkenyl, alkynyl, C(O)H, C(O) alkyl, C(O)alkenyl, C(O)alkynyl, C(O)OH, C(O) Oalkyl, C(O)cycloalkyl, C(O)heterocyclyl, C(O) aryl, C(O)heteroaryl, $NH_2$, OH, O(alkyl), cycloalkyl, cycloalkenyl, cycloalkynyl, and aryl; or $R_4$ and $R_5$, taken together with the nitrogen atom to which they are attached, form a heterocyclyl or heteroaryl, wherein the heterocyclyl or heteroaryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O) OH, C(O)Oalkyl, C(O)cycloalkyl, C(O)heterocyclyl, C(O)aryl, C(O)heteroaryl, $NH_2$, OH, O(alkyl), cycloalkyl, cycloalkenyl, cycloalkynyl, and aryl.

2. The compound according to claim 1, or a pharmaceutically acceptable salt thereof, wherein:

$R_1$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, Si(alkyl)$_3$, Si(phenyl)$_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, Si(alkyl)$_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl; and wherein the phenyl of benzyl, C(O)cycloalkyl, C(O) heterocyclyl, C(O)aryl, C(O)heteroaryl, Si(phenyl)$_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $CH_3$, $CH_2CH_3$, $CH_2F$, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl;

$R_2$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, Si(alkyl)$_3$, Si(phenyl)$_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, Si(alkyl)$_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl; and wherein the phenyl of benzyl, C(O)cycloalkyl, C(O) heterocyclyl, C(O)aryl, C(O)heteroaryl, Si(phenyl)$_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $CH_3$, $CH_2CH_3$, $CH_2F$, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl;

$R_4$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, Si(alkyl)$_3$, Si(phenyl)$_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, Si(alkyl)$_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl; and wherein the phenyl of benzyl, C(O)cycloalkyl, C(O) heterocyclyl, C(O)aryl, C(O)heteroaryl, Si(phenyl)$_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $CH_3$, $CH_2CH_3$, $CH_2F$, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl; and $R_5$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl; and wherein the phenyl of benzyl, C(O)cycloalkyl, C(O) heterocyclyl, C(O)aryl, C(O)heteroaryl, $Si(phenyl)_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $CH_3$, $CH_2CH_3$, $CH_2F$, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $OCH_3$, cycloalkyl, cycloalkenyl, cycloalkynyl, and aryl.

3. The compound according to claim 1, or a pharmaceutically acceptable salt thereof, wherein:

$R_1$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)$OC_3$-C20 alkyl, C(O) cycloalkyl, C(O)heterocyclyl, C(O)aryl, C(O)heteroaryl, $NH_2$, OH, and $C_6$-C20 aryl; and wherein the phenyl of benzyl, C(O)cycloalkyl, C(O) heterocyclyl, C(O)aryl, C(O)heteroaryl, $Si(phenyl)_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $C_1$-C20 alkyl, C1-C20 haloalkyl, $C_2$-C20 alkenyl, $C_2$-C20 alkynyl, C(O)H, C(O)alkyl, C(O)alkenyl, C(O)alkynyl, C(O)OH, C(O)$OC_3$-C20 alkyl, C(O)cycloalkyl, C(O)heterocyclyl, C(O)aryl, C(O)heteroaryl, $NH_2$, OH, and $C_6$-C20 aryl;

$R_2$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)$OC_3$-C20 alkyl, C(O) cycloalkyl, C(O)heterocyclyl, C(O)aryl, C(O)heteroaryl, $NH_2$, OH, and $C_6$-C20 aryl; and wherein the phenyl of benzyl, C(O)cycloalkyl, C(O) heterocyclyl, C(O)aryl, C(O)heteroaryl, $Si(phenyl)_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, C1-C20 alkyl, C1-C20 haloalkyl, $C_2$-C20 alkenyl, $C_2$-C20 alkynyl, C(O)H, C(O)alkyl, C(O)alkenyl, C(O)alkynyl, C(O)OH, C(O)$OC_3$-C20 alkyl, C(O)cycloalkyl, C(O)heterocyclyl, C(O)aryl, C(O)heteroaryl, $NH_2$, OH, and $C_6$-C20 aryl; or $R_1$ and $R_2$, taken together with the nitrogen atom to which they are attached, form a heterocyclyl or heteroaryl, wherein the heterocyclyl or heteroaryl is optionally substituted with one or more substituents independently selected from the group consisting of halogen, CN, $NO_2$, $C_1$-C20 alkyl, C1-C20 haloalkyl, $C_2$-$C_{20}$ alkenyl, $C_2$-C20 alkynyl, C(O)H, C(O)alkyl, C(O)alkenyl, C(O)alkynyl, C(O)OH, C(O)$OC_3$-C20 alkyl, C(O)cycloalkyl, C(O)heterocyclyl, C(O)aryl, C(O)heteroaryl, $NH_2$, OH, and $C_6$-C20 aryl;

$R_4$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, $Si(alkyl)_3$, $Si(phenyl)_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, $Si(alkyl)_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)$OC_3$-C20 alkyl, C(O) cycloalkyl, C(O)heterocyclyl, C(O)aryl, C(O)heteroaryl, $NH_2$, OH, and $C_6$-C20 aryl; and wherein the phenyl of benzyl, C(O)cycloalkyl, C(O) heterocyclyl, C(O)aryl, C(O)heteroaryl, $Si(phenyl)_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $C_1$-C20 alkyl, C1-C20 haloalkyl, $C_2$-C20 alkenyl, $C_2$-C20 alkynyl, C(O)H, C(O)alkyl, C(O)alkenyl, C(O)alkynyl, C(O)OH, C(O)O$C_3$-C20 alkyl, C(O)cycloalkyl, C(O)heterocyclyl, C(O)aryl, C(O)heteroaryl, $NH_2$, OH, and $C_6$-C20 aryl; and $R_5$ is H, halogen, alkyl, haloalkyl, benzyl, alkenyl, alkynyl, C(O)H, C(O)alkyl, C(O)alkenyl, C(O)alkynyl, C(O)OH, C(O)cycloalkyl, C(O)heterocyclyl, C(O)aryl, C(O)heteroaryl, Si(alkyl)$_3$, Si(phenyl)$_3$, O(alkyl), O(benzyl), $S(O)_2$alkyl, $S(O)_2$alkenyl, $S(O)_2$alkynyl, $S(O)_2$cycloalkyl, $S(O)_2$heterocyclyl, $S(O)_2$aryl, $S(O)_2$heteroaryl, cycloalkyl, or aryl;

wherein the alkyl, haloalkyl, $CH_2$ of benzyl, alkenyl, alkynyl, C(O)H, C(O)alkyl, C(O)alkenyl, C(O)alkynyl, Si(alkyl)$_3$, O(alkyl), $CH_2$ of O(benzyl), $S(O)_2$alkyl, $S(O)_2$alkenyl, or $S(O)_2$alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)O$C_3$-C20 alkyl, C(O) cycloalkyl, C(O)heterocyclyl, C(O)aryl, C(O)heteroaryl, $NH_2$, OH, and $C_6$-C20 aryl; and wherein the phenyl of benzyl, C(O)cycloalkyl, C(O) heterocyclyl, C(O)aryl, C(O)heteroaryl, Si(phenyl)$_3$, phenyl of O(benzyl), $S(O)_2$cycloalkyl, $S(O)_2$heterocyclyl, $S(O)_2$aryl, $S(O)_2$heteroaryl, cycloalkyl, or aryl is optionally substituted with one or more substituents independently selected from the group consisting of halogen, CN, $NO_2$, $C_1$-C20 alkyl, C1-C20 haloalkyl, $C_2$-C20 alkenyl, $C_2$-C20 alkynyl, C(O)H, C(O)alkyl, C(O)alkenyl, C(O)alkynyl, C(O)OH, C(O)O$C_3$-C20 alkyl, C(O)cycloalkyl, C(O)heterocyclyl, C(O)aryl, C(O)heteroaryl, $NH_2$, OH, and $C_6$-C20 aryl; or $R_4$ and $R_5$, taken together with the nitrogen atom to which they are attached, form a heterocyclyl or heteroaryl, wherein the heterocyclyl or heteroaryl is optionally substituted with one or more substituents independently selected from the group consisting of halogen, CN, $NO_2$, $C_1$-C20 alkyl, C1-C20 haloalkyl, $C_2$-$C_{20}$ alkenyl, $C_2$-C20 alkynyl, C(O)H, C(O)alkyl, C(O)alkenyl, C(O)alkynyl, C(O)OH, C(O)O$C_3$-C20 alkyl, C(O)cycloalkyl, C(O)heterocyclyl, C(O)aryl, C(O)heteroaryl, $NH_2$, OH, and $C_6$-C20 aryl.

4. The compound according to claim 1, or a pharmaceutically acceptable salt thereof, wherein:

$R_1$ is H, halogen, $C_1$-C20 alkyl, $C_1$-C20 haloalkyl, benzyl, $C_3$-C20 alkenyl, $C_3$-C20 alkynyl, C(O)$C_1$-$C_{20}$ alkyl, C(O)$C_2$-C20 alkenyl, C(O)$C_2$-C20 alkynyl, C(O)$C_3$-C20 cycloalkyl, Si($C_1$-$C_9$ alkyl)$_3$, Si(phenyl)$_3$, O($C_1$-$C_{20}$ alkyl), O(benzyl), $S(O)_2C_1$-C20 alkyl, $S(O)_2C_2$-C20 alkenyl, $S(O)_2C_2$-C20 alkynyl, $S(O)_2C_3$-C20 cycloalkyl, $C_3$-C20 cycloalkyl, or $C_6$-C20 aryl;

wherein the $C_1$-C20 alkyl, $C_1$-C20 haloalkyl, $CH_2$ of benzyl, $C_3$-C20 alkenyl, $C_3$-C20 alkynyl, C(O)$C_1$-$C_{20}$ alkyl, C(O)$C_2$-C20 alkenyl, C(O)$C_2$-C20 alkynyl, Si($C_1$-$C_9$ alkyl)$_3$, O($C_1$-C20 alkyl), $CH_2$ of O(benzyl), $S(O)_2C_1$-C20 alkyl, $S(O)_2C_2$-C20 alkenyl, or $S(O)_2C_2$-C20 alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)O$C_3$-C20 alkyl, C(O)cycloalkyl, C(O)heterocyclyl, C(O)aryl, C(O)heteroaryl, $NH_2$, OH, and aryl; and wherein the phenyl of benzyl, C(O)$C_3$-C20 cycloalkyl, Si(phenyl)$_3$, phenyl of O(benzyl), $SS(O)_2C_3$-$C_{20}$ cycloalkyl, $C_3$-C20 cycloalkyl, or $C_6$-C20 aryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O) OH, C(O)Oalkyl, C(O)cycloalkyl, C(O)heterocyclyl, C(O)aryl, C(O)heteroaryl, $NH_2$, OH, and aryl;

$R_2$ is H, halogen, $C_1$-C20 alkyl, $C_1$-C20 haloalkyl, benzyl, $C_3$-C20 alkenyl, $C_3$-C20 alkynyl, C(O)$C_1$-$C_{20}$ alkyl, C(O)$C_2$-C20 alkenyl, C(O)$C_2$-C20 alkynyl, C(O)$C_3$-C20 cycloalkyl, Si($C_1$-$C_9$ alkyl)$_3$, Si(phenyl)$_3$, O($C_1$-$C_{20}$ alkyl), O(benzyl), $S(O)_2C_1$-C20 alkyl, $S(O)_2C_2$-C20 alkenyl, $S(O)_2C_2$-C20 alkynyl, $S(O)_2C_3$-C20 cycloalkyl, $C_3$-C20 cycloalkyl, or $C_6$-C20 aryl;

wherein the $C_1$-C20 alkyl, $C_1$-C20 haloalkyl, $CH_2$ of benzyl, $C_3$-C20 alkenyl, $C_3$-C20 alkynyl, C(O)$C_1$-$C_{20}$ alkyl, C(O)$C_2$-C20 alkenyl, C(O)$C_2$-C20 alkynyl, Si($C_1$-$C_9$ alkyl)$_3$, O($C_1$-C20 alkyl), $CH_2$ of O(benzyl), $S(O)_2C_1$-C20 alkyl, $S(O)_2C_2$-C20 alkenyl, or $S(O)_2C_2$-C20 alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)O$C_3$-C20 alkyl, C(O)cycloalkyl, C(O)heterocyclyl, C(O)aryl, C(O)heteroaryl, $NH_2$, OH, and aryl; and wherein the phenyl of benzyl, C(O)$C_3$-C20 cycloalkyl, Si(phenyl)$_3$, phenyl of O(benzyl), $SS(O)_2C_3$-$C_{20}$ cycloalkyl, $C_3$-C20 cycloalkyl, or $C_6$-C20 aryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O) OH, C(O)Oalkyl, C(O)cycloalkyl, C(O)heterocyclyl, C(O)aryl, C(O)heteroaryl, $NH_2$, OH, and aryl; or $R_1$ and $R_2$, taken together with the nitrogen atom to which they are attached, form a heterocyclyl or heteroaryl, wherein the heterocyclyl or heteroaryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O)OH, C(O) Oalkyl, C(O)cycloalkyl, C(O)heterocyclyl, C(O)aryl, C(O)heteroaryl, $NH_2$, OH, and aryl;

$R_4$ is H, halogen, $C_1$-C20 alkyl, $C_1$-C20 haloalkyl, benzyl, $C_3$-C20 alkenyl, $C_3$-C20 alkynyl, C(O)$C_1$-$C_{20}$ alkyl, C(O)$C_2$-C20 alkenyl, C(O)$C_2$-C20 alkynyl, C(O)$C_3$-C20 cycloalkyl, Si($C_1$-$C_9$ alkyl)$_3$, Si(phenyl)$_3$, O($C_1$-$C_{20}$ alkyl), O(benzyl), $S(O)_2C_1$-C20 alkyl, $S(O)_2C_2$-C20 alkenyl, $S(O)_2C_2$-C20 alkynyl, $S(O)_2C_3$-C20 cycloalkyl, $C_3$-C20 cycloalkyl, or $C_6$-C20 aryl;

wherein the $C_1$-C20 alkyl, $C_1$-C20 haloalkyl, $CH_2$ of benzyl, $C_3$-C20 alkenyl, $C_3$-C20 alkynyl, C(O)$C_1$-$C_{20}$ alkyl, C(O)$C_2$-C20 alkenyl, C(O)$C_2$-C20 alkynyl, Si($C_1$-$C_9$ alkyl)$_3$, O($C_1$-C20 alkyl), $CH_2$ of O(benzyl), $S(O)_2C_1$-C20 alkyl, $S(O)_2C_2$-C20 alkenyl, or $S(O)_2C_2$-C20 alkynyl is optionally substituted with one or more substituents independently selected from the group consisting of halogen, CN, $NO_2$, C(O)H, C(O)alkyl, C(O)alkenyl, C(O)alkynyl, C(O)OH, C(O)O$C_3$-C20 alkyl, C(O)cycloalkyl, C(O)heterocyclyl, C(O)aryl, C(O)heteroaryl, $NH_2$, OH, and aryl; and wherein the phenyl of benzyl, C(O)$C_3$-C20 cycloalkyl, Si(phenyl)$_3$, phenyl of O(benzyl), $SS(O)_2C_3$-$C_{20}$ cycloalkyl, $C_3$-C20 cycloalkyl, or $C_6$-C20 aryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, and aryl; and $R_5$ is H, halogen, $C_1$-C20 alkyl, $C_1$-C20 haloalkyl, benzyl, $C_3$-C20 alkenyl, $C_3$-C20 alkynyl, $C(O)C_1$-$C_{20}$ alkyl, $C(O)C_2$-C20 alkenyl, $C(O)C_2$-C20 alkynyl, $C(O)C_3$-C20 cycloalkyl, $Si(C_1$-$C_9$ alkyl$)_3$, Si(phenyl$)_3$, $O(C_1$-$C_{20}$ alkyl), O(benzyl), $S(O)_2C_1$-C20 alkyl, $S(O)_2C_2$-C20 alkenyl, $S(O)_2C_2$-C20 alkynyl, $S(O)_2C_3$-C20 cycloalkyl, $C_3$-C20 cycloalkyl, or $C_6$-C20 aryl;

wherein the $C_1$-C20 alkyl, $C_1$-C20 haloalkyl, $CH_2$ of benzyl, $C_3$-C20 alkenyl, $C_3$-C20 alkynyl, $C(O)C_1$-$C_{20}$ alkyl, $C(O)C_2$-C20 alkenyl, $C(O)C_2$-C20 alkynyl, $Si(C_1$-$C_9$ alkyl$)_3$, $O(C_1$-C20 alkyl), $CH_2$ of O(benzyl), $S(O)_2C_1$-C20 alkyl, $S(O)_2C_2$-C20 alkenyl, or $S(O)_2C_2$-C20 alkynyl is optionally substituted with one or more substituents independently selected from the group consisting of halogen, CN, $NO_2$, C(O)H, C(O)alkyl, C(O)alkenyl, C(O)alkynyl, C(O)OH, $C(O)OC_3$-C20 alkyl, C(O)cycloalkyl, C(O)heterocyclyl, C(O)aryl, C(O)heteroaryl, $NH_2$, OH, and aryl; and wherein the phenyl of benzyl, $C(O)C_3$-C20 cycloalkyl, Si(phenyl$)_3$, phenyl of O(benzyl), $SS(O)_2C_3$-$C_{20}$ cycloalkyl, $C_3$-C20 cycloalkyl, or C6-C20 aryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, and aryl; or $R_4$ and $R_5$, taken together with the nitrogen atom to which they are attached, form a heterocyclyl or heteroaryl, wherein the heterocyclyl or heteroaryl is optionally substituted with one or more substituents independently selected from the group consisting of halogen, CN, $NO_2$, alkyl, haloalkyl, alkenyl, alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, and aryl.

5. The compound according to claim 1, or a pharmaceutically acceptable salt thereof, wherein:

$R_7$ is H, halogen, CN, $NO_2$, $C_1$-$C_{10}$ alkyl, $C_1$-$C_{10}$ haloalkyl, $C_2$-$C_{10}$ alkenyl, $C_2$-$C_{10}$ alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $O(C_1$-$C_{10}$ alkyl), cycloalkyl, cycloalkenyl, cycloalkynyl, or aryl;

$R_6$ is H, halogen, CN, $NO_2$, $C_1$-$C_{10}$ alkyl, $C_1$-$C_{10}$ haloalkyl, $C_2$-$C_{10}$ alkenyl, $C_2$-$C_{10}$ alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $O(C_1$-$C_{10}$ alkyl), cycloalkyl, cycloalkenyl, cycloalkynyl, or aryl; and $R_3$ is H, halogen, CN, $NO_2$, $C_1$-$C_{10}$ alkyl, $C_1$-$C_{10}$ haloalkyl, $C_2$-$C_{10}$ alkenyl, $C_2$-$C_{10}$ alkynyl, C(O)H, C(O)alkyl, C(O)alkenyl, C(O)alkynyl, C(O)OH, C(O)Oalkyl, C(O)cycloalkyl, C(O)heterocyclyl, C(O)aryl, C(O)heteroaryl, $NH_2$, OH, $O(C_1$-$C_{10}$ alkyl), cycloalkyl, cycloalkenyl, cycloalkynyl, or aryl.

6. The compound according to claim 1, wherein the compound is of formula II:

II

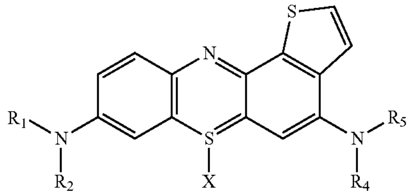

or a pharmaceutically acceptable salt thereof.

7. A pharmaceutical composition comprising at least one pharmaceutically acceptable carrier or excipient and the compound according to claim 1, or a pharmaceutically acceptable salt thereof.

8. The pharmaceutical composition according to claim 7, wherein the pharmaceutical composition comprises at least one pharmaceutically acceptable excipient selected from the group consisting of a diluent, a filler, a lubricant, a preservative, and a wetting agent, or a combination thereof.

9. The pharmaceutical composition according to claim 7, wherein the pharmaceutical composition is further formulated as a dosage form selected from the group consisting of an aerosol, a capsule, a cataplasm, a drop, a gel spray, a granule, an injection, a medicinal liquor, a mucosal preparation, an oral liquid, an oral lozenge, a paste, a patch, a pellet, a pill, a smearing preparation, a suspension, a tablet, and a tincture.

* * * * *